(12) United States Patent
Wurster et al.

(10) Patent No.: US 9,321,766 B1
(45) Date of Patent: Apr. 26, 2016

(54) KINASE INHIBITORS

(71) Applicant: Allergan, Inc., Irvine, CA (US)

(72) Inventors: Julie Wurster, Irvine, CA (US); Richard Yee, Tustin, CA (US); Clarence Eugene Hull, III, Mission Viejo, CA (US); Thomas C. Malone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/507,782

(22) Filed: Oct. 6, 2014

(51) Int. Cl.
| | | |
|---|---|---|
| *C07D 487/04* | (2006.01) | |
| *C07D 403/04* | (2006.01) | |
| *C07D 401/04* | (2006.01) | |
| *A61K 31/519* | (2006.01) | |
| *C07D 471/04* | (2006.01) | |
| *A61P 19/04* | (2006.01) | |
| *A61P 35/00* | (2006.01) | |

(52) U.S. Cl.
CPC ............ *C07D 471/04* (2013.01); *A61K 31/519* (2013.01); *C07D 401/04* (2013.01); *C07D 403/04* (2013.01); *C07D 487/04* (2013.01)

(58) Field of Classification Search
CPC .. C07D 487/04; C07D 403/04; C07D 401/04; A61K 31/519
USPC ................................ 544/279, 280; 514/258.1
See application file for complete search history.

(56) References Cited

U.S. PATENT DOCUMENTS

| | | | |
|---|---|---|---|
| 8,691,827 | B2 | 4/2014 | Breslin et al. |
| 2007/0054916 | A1 | 3/2007 | Patel et al. |
| 2008/0249090 | A1 | 10/2008 | Hu et al. |
| 2010/0130465 | A1 | 5/2010 | Shipps, Jr. et al. |
| 2010/0249030 | A1 | 9/2010 | Basso-Porcaro |
| 2013/0237537 | A1 | 9/2013 | Hull, III et al. |
| 2013/0237538 | A1 | 9/2013 | Hull, III et al. |

FOREIGN PATENT DOCUMENTS

WO 2011101806 A1 8/2011

OTHER PUBLICATIONS

Cross, L.C., et al., Rules for the Nomenclature of Organic Chemistry, Section E: Stereochemistry, International Union of Pure and Applied Chemistry 1976, 45: 11-13.
Nobuo Jo, Carolina Mailhos,et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, Jun. 2006.
Justine R Smith, et al., Expression of vascular endothelial growth factor and its receptors in rosacea, Br J Ophthalmol 2007;91:226-229. doi: 10.1136/bjo.2006.101121.
S. W. Cowan-Jacob, et al., Structural biology of protein tyrosine kinases, Cell. Mol. Life Sci. 63 (2006) 2608-2625.
Regina Heidenreich, et al., Angiogenesis: The New Potential Target for the Therapy of Psoriasis?Drug News Perspect 21(2), Mar. 2008.
Aimee V. Chappelow et al., Neovascular Age-Related Macular Degeneration, Potential Therapies, Drugs 2008; 68 (8): 1029-1036.
Mark Rami Barakat, et al., VEGF inhibitors for the treatment of neovascular age-related macular degeneration, Expert Opin. Investig. Drugs (2009) 18(5).
Xinyuan Zhang, et al., Vascular endothelial growth factor-A: A multifunctional molecular player in diabetic retinopathy, The International Journal of Biochemistry & Cell Biology 41 (2009) 2368-2371.
Zhang Ni, et al., Emerging Pharmacologic Therapies for Wet Age-Related Macular Degeneration, Ophthalmologica 2009;223:401-410.
Jayne M. Stommel et al., Coactivation of Receptor Tyrosine Kinases Affects the Response of Tumor Cells to Targeted Therapies, www.sciencemag.org Science vol. 318 Oct. 12, 2007.

*Primary Examiner* — Venkataraman Balasubramanian
(74) *Attorney, Agent, or Firm* — Jonathan Bass

(57) ABSTRACT

The present invention relates to organic molecules capable of modulating tyrosine kinase signal transduction in order to regulate, modulate and/or inhibit abnormal cell proliferation.

9 Claims, No Drawings

KINASE INHIBITORS

FIELD OF THE INVENTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

DESCRIPTION OF THE RELATED ART

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105), rosacea (Smith, J. R., V. B. Lanier, et al. Br J Ophthalmol 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFR may provide a greater therapeutic effect by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated tyrosine kinase signal transduction, including vascular proliferative disorders such as diabetic retinopathy, age-related macular degeneration and retinopathy of prematurity.

In one aspect, the invention provides a compound represented by Formula I or a pharmaceutically acceptable salt thereof or stereoisomeric forms thereof, or the enantiomers, diastereoisomers, tautomers, zwitterions and pharmaceutically acceptable salts thereof:

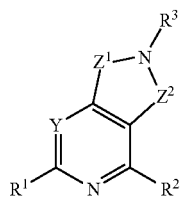

I wherein:
$R^1$ is hydrogen, substituted or unsubstituted $C_{1-12}$ alkyl, halogen, $NR^9R^{10}$, $C(O)NR^9R^{10}$, $(CR^{11}R^{12})_pNR^9R^{10}$, $(CR^{11}R^{12})_pC(O)OR^{13}$, $(CR^{11}R^{12})_pOR^{13}$, $NR^9C(O)(CR^{11}R^{12})_pNR^9R^{10}$, $NR^9C(O)(CR^{11}R^{12})_pC(O)OR^{13}$, $NR^9C(O)(CR^{11}R^{12})_pOR^{13}$, $C(O)(CR^{11}R^{12})_pNR^9R^{10}$, $C(O)(CR^{11}R^{12})_pC(O)OR^{13}$, $C(O)(CR^{11}R^{12})_pCOR^{13}$, $C(O)NR^9(CR^{11}R^{12})_pNR^9R^{10}$, $C(O)NR^9(CR^{11}R^{12})_pC(O)OR^{13}$, $C(O)NR^9(CR^{11}R^{12})_pCOR^{13}$, $NR^9C(O)NR^{10}(CR^{11}R^{12})_pNR^9R^{10}$, $NR^9C(O)NR^{10}(CR^{11}R^{12})_pC(O)OR^{13}$ or $NR^9C(O)NR^{10}(CR^{11}R^{12})_pOR^{13}$;
$R^2$ is hydrogen or $NH_2$;
$R^3$ is represented by one of the formulae below

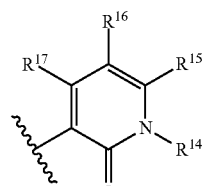

II

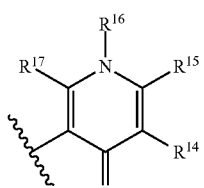

III

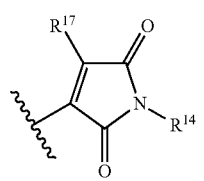

IV

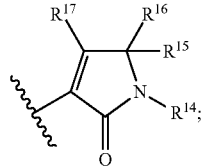

V $Z^1$ is $(CR^4R^5)_n$;
$Z^2$ is $(CR^6R^7)_m$;
Y is $CR^8$ or N;
n is 1 or 2;
m is 1 or 2;
p is 0, 1, 2, 3, 4, 5 or 6;
t is 0, 1, 2, 3, 4, 5 or 6;
u is 1, 2, 3, 4, 5 or 6;
$R^4$ is hydrogen or substituted or unsubstituted $C_{1-12}$ alkyl;
$R^5$ is hydrogen or substituted or unsubstituted $C_{1-12}$ alkyl;
$R^6$ is hydrogen or substituted or unsubstituted $C_{1-12}$ alkyl;
$R^7$ is hydrogen or substituted or unsubstituted $C_{1-12}$ alkyl;
$R^8$ is hydrogen, halogen, trifluoromethyl, substituted or unsubstituted $C_{1-12}$ alkyl, $(CR^{20}R^{21})_tNR^{18}R^{19}$, $(CR^{20}R^{21})_tC(O)OR^{22}$, $(CR^{20}R^{21})_tOR^{22}$, $O(CR^{20}R^{21})_uNR^{18}R^{19}$, $O(CR^{20}R^{21})_tC(O)OR^{22}$, $O(CR^{20}R^{21})_uOR^{22}$, $NR^{18}(CR^{20}R^{21})_uNR^{18}R^{19}$, $NR^{18}(CR^{20}R^{21})_tC(O)OR^{22}$, $NR^{18}(CR^{20}R^{21})_uOR^{22}$, $C(O)(CR^{20}R^{21})_tNR^{18}R^{19}$, $C(O)(CR^{20}R^{21})_tC(O)OR^{22}$, $C(O)(CR^{20}R^{21})_tCOR^{22}$, $NR^{18}C(O)(CR^{20}R^{21})_tNR^{18}R^{19}$, $NR^{18}C(O)(CR^{20}R^{21})_tC(O)OR^{22}$, $R^{18}C(O)(CR^{20}R^{21})_tOR^{22}$, $C(O)NR^{18}(CR^{20}R^{21})_uNR^{18}R^{19}$, $C(O)NR^{18}(CR^{20}R^{21})_tC(O)OR^{22}$, $C(O)NR^{18}(CR^{20}R^{21})_tCOR^{22}$, $NR^{18}C(O)NR^{19}(CR^{20}R^{21})_uNR^{18}R^{19}$, $NR^{18}C(O)NR^{19}(CR^{20}R^{21})_tC(O)OR^{22}$ or $NR^{18}C(O)NR^{19}(CR^{20}R^{21})_uOR^{22}$;
$R^9$ is hydrogen, substituted or unsubstituted $C_{1-12}$ alkyl, substituted or unsubstituted aryl, or together with the N and $R^{10}$ can form a substituted or unsubstituted heterocyclic ring;
$R^{10}$ is hydrogen, substituted or unsubstituted $C_{1-12}$ alkyl or together with the N and $R^9$ can form a substituted or unsubstituted heterocyclic ring;
$R^{11}$ is hydrogen, substituted or unsubstituted $C_{1-12}$ alkyl halogen, trifluoromethyl, or hydroxyl;
$R^{12}$ is hydrogen, substituted or unsubstituted $C_{1-12}$ alkyl, halogen, trifluoromethyl or hydroxyl;
$R^{13}$ is hydrogen or substituted or unsubstituted $C_{1-12}$ alkyl;
$R^{14}$ is substituted or unsubstituted $C_{1-12}$ alkyl, substituted or unsubstituted heterocycle or substituted or unsubstituted aryl;
$R^{15}$ is hydrogen, substituted or unsubstituted $C_{1-12}$ alkyl, halogen or trifluoromethyl;
$R^{16}$ is hydrogen, substituted or unsubstituted $C_{1-12}$ alkyl, halogen or trifluoromethyl;
$R^{17}$ is hydrogen, substituted or unsubstituted $C_{1-12}$ alkyl, halogen or trifluoromethyl;
$R^{18}$ is hydrogen, substituted or unsubstituted $C_{1-12}$ alkyl, aryl or together with the N and $R^{19}$ can form a substituted or unsubstituted heterocyclic ring;
$R^{19}$ is hydrogen or substituted or unsubstituted $C_{1-12}$ alkyl or together with the N and $R^{18}$ can form a substituted or unsubstituted heterocyclic ring;
$R^{20}$ is hydrogen, substituted or unsubstituted $C_{1-12}$ alkyl, halogen, trifluoromethyl or hydroxyl;
$R^{21}$ is hydrogen, substituted or unsubstituted $C_{1-12}$ alkyl, halogen, trifluoromethyl or hydroxyl;
$R^{22}$ is hydrogen or substituted or unsubstituted $C_{1-12}$ alkyl; and
with the proviso that m and n cannot be 2 in same time.

In another aspect, the invention provides a compound represented by Formula I
wherein:
$R^1$ is $NR^9R^{10}$;
$R^2$ is hydrogen;
$R^3$

II

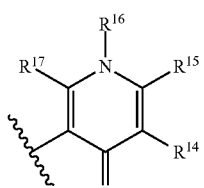

$Z^1$ is $(CR^4R^5)_n$;
$Z^2$ is $(CR^6R^7)_m$;

Y is N;
n is 2;
m is 1;
p is 0, 1, 2, 3, 4, 5 or 6;
$R^4$ is hydrogen or substituted or unsubstituted $C_{1-12}$ alkyl;
$R^5$ is hydrogen or substituted or unsubstituted $C_{1-12}$ alkyl;
$R^6$ is hydrogen or substituted or unsubstituted $C_{1-12}$ alkyl;
$R^7$ is hydrogen or substituted or unsubstituted $C_{1-12}$ alkyl;
$R^9$ is hydrogen, substituted or unsubstituted $C_{1-12}$ alkyl, substituted or unsubstituted aryl, or together with the N and $R^{10}$ can form a substituted or unsubstituted heterocyclic ring;
$R^{10}$ is hydrogen, substituted or unsubstituted $C_{1-12}$ alkyl or together with the N and $R^9$ can form a substituted or unsubstituted heterocyclic ring;
$R^{14}$ is hydrogen, substituted or unsubstituted $C_{1-12}$ alkyl, substituted or unsubstituted heterocycle or substituted or unsubstituted aryl;
$R^{15}$ is hydrogen;
$R^{16}$ is hydrogen;
$R^{17}$ is hydrogen or substituted or unsubstituted $C_{1-12}$ alkyl.

In another aspect, the invention provides a compound represented by Formula I
wherein:
$R^1$ is $NR^9R^{10}$;
$R^2$ is hydrogen;
$R^3$ is

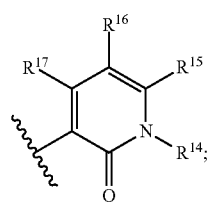

II $Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is hydrogen;
$R^{15}$ is hydrogen;
$R^{16}$ is hydrogen;
$R^{17}$ is hydrogen.

In another aspect, the invention provides a compound represented by Formula I
wherein:
$R^1$ is $NR^9R^{10}$;
$R^2$ is hydrogen;
$R^3$ is

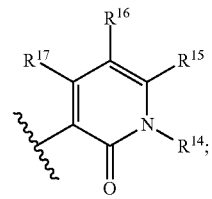

II $Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is substituted or unsubstituted $C_{1-12}$ alkyl;
$R^{15}$ is hydrogen;
$R^{16}$ is hydrogen;
$R^{17}$ is hydrogen.

In another aspect, the invention provides a compound represented by Formula I
wherein:
$R^1$ is $NR^9R^{10}$;
$R^2$ is hydrogen;
$R^3$ is

II $Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is hydrogen;
$R^{15}$ is hydrogen;
$R^{16}$ is hydrogen;
$R^{17}$ is $C_{1-12}$ alkyl.

In another aspect, the invention provides a compound represented by Formula I
wherein:
$R^1$ is $NR^9R^{10}$;
$R^2$ is hydrogen;

$R^3$ is

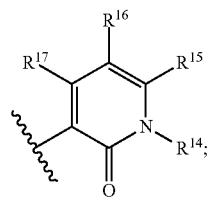

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is substituted or unsubstituted $C_{1-12}$ alkyl;
$R^{10}$ is hydrogen;
$R^{14}$ is substituted or unsubstituted $C_{1-12}$ alkyl;
$R^{15}$ is hydrogen;
$R^{16}$ is hydrogen;
$R^{17}$ is substituted or unsubstituted $C_{1-12}$ alkyl.

In another aspect, the invention provides a compound represented by Formula I
wherein:
$R^1$ is $NR^9R^{10}$;
$R^2$ is hydrogen; $R^3$ is

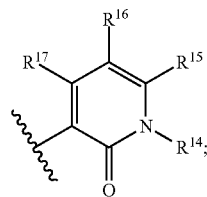

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is $C_{1-12}$ alkyl;
$R^{14}$ is substituted or unsubstituted heterocycle I;
$R^{15}$ is hydrogen;
$R^{16}$ is hydrogen;
$R^{17}$ is substituted or unsubstituted $C_{1-12}$ alkyl.

In another aspect, the invention provides a compound represented by Formula I
wherein:
$R^1$ is $NR^9R^{10}$;
$R^2$ is hydrogen;

$R^3$ is

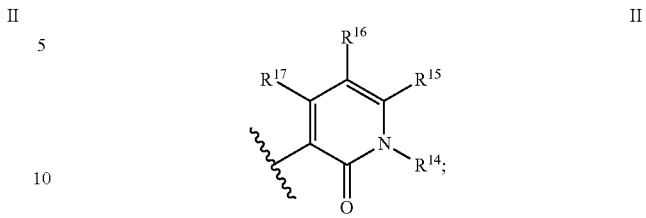

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is substituted or unsubstituted $C_{1-12}$ alkyl;
$R^{10}$ is hydrogen;
$R^{14}$ is substituted or unsubstituted aryl;
$R^{15}$ is hydrogen;
$R^{16}$ is hydrogen;
$R^{17}$ is substituted or unsubstituted $C_{1-12}$ alkyl.

The term "alkyl", as used herein, refers to saturated, monovalent or divalent hydrocarbon moieties having linear or branched moieties or combinations thereof and containing 1 to 12 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, ketone groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amide groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—CH$_2$—) group, of the alkenyl can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. C$_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—CH$_2$—) group, of the alkynyl can be replaced by oxygen, sulfur, sulfoxide, nitrogen, carbonyl, carboxyl, sulfonyl, sulfate, sulfonate, amide, sulfonamide, by a divalent C$_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —OC$_{1-6}$ alkyl groups, —SC$_{1-6}$ alkyl groups, —C$_{1-8}$ alkyl groups, —C$_{2-6}$ alkenyl groups, —C$_{2-6}$ alkynyl groups, amide groups, ketone groups, alkylamino groups, amino groups, aryl groups, ester groups, ketone groups, carboxylic acid groups, C$_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl C$_{1-6}$ alkyl groups, sulfoxide C$_{1-6}$ alkyl groups, sulfonamide groups, carboxcyclic acid groups, C$_{1-6}$ alkyl carboxylates (ester) groups, amide groups, nitro groups, cyano groups, —OC$_{1-6}$ alkyl groups, —SC$_{1-6}$ alkyl groups, —C$_{1-6}$ alkyl groups, —C$_{2-6}$ alkenyl groups,—C$_{2-6}$ alkynyl groups, ketone groups, aldehydes, alkylamino groups, amino groups, aryl groups, C$_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)R$^x$ wherein R$^x$ can be alkyl, aryl, cycloalkyl, cycloalkenyl, heterocycle as defined above.

The term "ester" as used herein, represents an organic compound having a carbonyl group linked to a carbon atom such as —C(O)OR$^x$ wherein R$^x$ can be alkyl, aryl, cycloalkyl, cycloalkenyl, heterocycle as defined above.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," or "NR$^x$R$^y$C(O)" wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.
Other defined terms are used throughout this specification:
"Ac" refers to acetyl
"Et" refers to ethyl
"iPr" refers to i-propyl
"Me" refers to methyl
"MeOH" refers to methanol
"PDGF" refers to platelet derived growth factor
"Ph" refers to phenyl
"PTKs" refers to protein tyrosine kinase
"RTKs" refers to receptor tyrosine kinase
"rt" refers to room temperature
"tBu" refers to t-butyl.
"THF" refers to tetrahydrofuran
"VEGF" refers to vascular endothelial growth factor
"VEGFR" refers to vascular endothelial growth factor receptor
Some compounds of the invention are:
3-(2-amino-7,8-dihydropyrido[4,3-d]pyrimidin-6(5H)-yl)-1-(4-(tert-butyl)phenyl)pyridin-2(1H)-one;
3-(2-amino-7,8-dihydropyrido[4,3-d]pyrimidin-6(5H)-yl)-1-(4-tert-butylphenyl)-4-methylpyridin-2(1H)-one;
3-(2-amino-7,8-dihydropyrido[4,3-d]pyrimidin-6(5H)-yl)-1-(4-methoxyphenyl)-4-methylpyridin-2(1H)-one;
3-(2-amino-7,8-dihydropyrido[4,3-d]pyrimidin-6(5H)-yl)-1-[4-(2-methoxyethyl)phenyl]-4-methylpyridin-2(1H)-one;
3-(2-amino-7,8-dihydropyrido[4,3-d]pyrimidin-6(5H)-yl)-4-methyl-1-(3-thienyl)pyridin-2(1H)-one;
3-(2-amino-7,8-dihydropyrido[4,3-d]pyrimidin-6(5H)-yl)-4-methyl-1-(1-methyl-1H-pyrazol-3-yl)-1,6-dihydropyridin-2(3H)-one;
3-(2-amino-7,8-dihydropyrido[4,3-d]pyrimidin-6(5H)-yl)-4-methyl-1-(m-tolyl)-1,6-dihydropyridin-2(3H)-one;
3-(2-amino-7,8-dihydropyrido[4,3-d]pyrimidin-6(5H)-yl)-4-methyl-1-(4-methylphenyl)pyridin-2(1H)-one;

3-(2-amino-7,8-dihydropyrido[4,3-d]pyrimidin-6(5H)-yl)-4-methyl-1-(2-methylphenyl)pyridin-2(1H)-one;

3-(2-amino-7,8-dihydropyrido[4,3-d]pyrimidin-6(5H)-yl)-1-(3-tert-butylphenyl)-4-methylpyridin-2(1H)-one;

3-(2-amino-7,8-dihydropyrido[4,3-d]pyrimidin-6(5H)-yl)-1-[4-(dimethylamino)phenyl]-4-methylpyridin-2(1H)-one;

3-(2-amino-7,8-dihydropyrido[4,3-d]pyrimidin-6(5H)-yl)-1-[3-(dimethylamino)phenyl]-4-methylpyridin-2(1H)-one;

tert-butyl {4-[3-(2-amino-7,8-dihydropyrido[4,3-d]pyrimidin-6(5H)-yl)-4-methyl-2-oxopyridin-1(2H)-yl]phenyl}carbamate;

3-(2-amino-7,8-dihydropyrido[4,3-d]pyrimidin-6(5H)-yl)-1-(4-aminophenyl)-4-methylpyridin-2(1H)-one;

N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide;

N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide;

tert-butyl {4-[3-(2-amino-7,8-dihydropyrido[4,3-d]pyrimidin-6(5H)-yl)-4-methyl-2-oxopyridin-1(2H)-yl]phenyl}carbamate;

3-(2-amino-7,8-dihydropyrido[4,3-d]pyrimidin-6(5H)-yl)-1-(4-aminophenyl)-4-methylpyridin-2(1H)-one;

N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide;

N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide;

N-{4-[3-(2-amino-7,8-dihydropyrido[4,3-d]pyrimidin-6(5H)-yl)-4-methyl-2-oxopyridin-1(2H)-yl]phenyl}-2-methylbenzamide;

N-{4-[3-(2-amino-7,8-dihydropyrido[4,3-d]pyrimidin-6(5H)-yl)-4-methyl-2-oxopyridin-1(2H)-yl]phenyl}-4-chlorobenzamide;

N-{4-[3-(2-amino-7,8-dihydropyrido[4,3-d]pyrimidin-6(5H)-yl)-4-methyl-2-oxopyridin-1(2H)-yl]phenyl}-3-chloro-4-fluorobenzamide;

N-{4-[3-(2-amino-7,8-dihydropyrido[4,3-d]pyrimidin-6(5H)-yl)-4-methyl-2-oxopyridin-1(2H)-yl]phenyl}-3-(methylthio)benzamide;

N-{4-[3-(2-amino-7,8-dihydropyrido[4,3-d]pyrimidin-6(5H)-yl)-4-methyl-2-oxopyridin-1(2H)-yl]phenyl}-4-chloro-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}benzamide;

N-{4-[3-(2-amino-7,8-dihydropyrido[4,3-d]pyrimidin-6(5H)-yl)-4-methyl-2-oxopyridin-1(2H)-yl]phenyl}-3-bromobenzamide;

N-{4-[3-(2-amino-7,8-dihydropyrido[4,3-d]pyrimidin-6(5H)-yl)-4-methyl-2-oxopyridin-1(2H)-yl]phenyl}-3-methoxybenzamide;

N-{4-[3-(2-amino-7,8-dihydropyrido[4,3-d]pyrimidin-6(5H)-yl)-4-methyl-2-oxopyridin-1(2H)-yl]phenyl}-3-methylthiophene-2-carboxamide;

N-{4-[3-(2-amino-7,8-dihydropyrido[4,3-d]pyrimidin-6(5H)-yl)-4-methyl-2-oxopyridin-1(2H)-yl]phenyl}-3-methylbenzamide;

N-{4-[3-(2-amino-7,8-dihydropyrido[4,3-d]pyrimidin-6(5H)-yl)-4-methyl-2-oxopyridin-1(2H)-yl]phenyl}-4-methylbenzamide;

N-{4-[3-(2-amino-7,8-dihydropyrido[4,3-d]pyrimidin-6(5H)-yl)-4-methyl-2-oxopyridin-1(2H)-yl]phenyl}-3,4-dimethylbenzamide;

N-{4-[3-(2-amino-7,8-dihydropyrido[4,3-d]pyrimidin-6(5H)-yl)-4-methyl-2-oxopyridin-1(2H)-yl]phenyl}-3-chloro-4-methoxybenzamide;

N-{4-[3-(2-amino-7,8-dihydropyrido[4,3-d]pyrimidin-6(5H)-yl)-4-methyl-2-oxopyridin-1(2H)-yl]phenyl}-2-fluoro-5-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-2-fluoro-5-methylbenzamide;

N-{4-[3-(2-amino-7,8-dihydropyrido[4,3-d]pyrimidin-6(5H)-yl)-4-methyl-2-oxopyridin-1(2H)-yl]phenyl}-5-tert-butylisoxazole-3-carboxamide;

N-{4-[3-(2-amino-7,8-dihydropyrido[4,3-d]pyrimidin-6(5H)-yl)-4-methyl-2-oxopyridin-1(2H)-yl]phenyl}-4-methoxy-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-3-(methylsulfinyl)benzamide;

3-[({4-[3-(2-amino-7,8-dihydropyrido[4,3-d]pyrimidin-6(5H)-yl)-4-methyl-2-oxopyridin-1(2H)-yl]phenyl}amino)carbonyl]benzoic acid;

3-{4-[({4-[3-(2-amino-7,8-dihydropyrido[4,3-d]pyrimidin-6(5H)-yl)-4-methyl-2-oxopyridin-1(2H)-yl]phenyl}amino)carbonyl]phenyl}propanoic acid;

N-{4-[3-(2-amino-7,8-dihydropyrido[4,3-d]pyrimidin-6(5H)-yl)-4-methyl-2-oxopyridin-1(2H)-yl]phenyl}-4-[(4-methylpiperazin-1-yl)methyl]-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-4-fluorobenzamide;

N-{4-[3-(2-amino-7,8-dihydropyrido[4,3-d]pyrimidin-6(5H)-yl)-4-methyl-2-oxopyridin-1(2H)-yl]phenyl}-3,4-dimethoxybenzamide;

N-{4-[3-(2-amino-7,8-dihydropyrido[4,3-d]pyrimidin-6(5H)-yl)-4-methyl-2-oxopyridin-1(2H)-yl]phenyl}-2-furamide;

N-{4-[3-(2-amino-7,8-dihydropyrido[4,3-d]pyrimidin-6(5H)-yl)-4-methyl-2-oxopyridin-1(2H)-yl]phenyl}-5-methyl-2-furamide;

4-[3-(2-amino-7,8-dihydropyrido[4,3-d]pyrimidin-6(5H)-yl)-4-methyl-2-oxopyridin-1(2H)-yl]-N-[(3-methyl-2-furyl)methyl]benzamide;

1-{4-[3-(2-amino-7,8-dihydropyrido[4,3-d]pyrimidin-6(5H)-yl)-4-methyl-2-oxopyridin-1(2H)-yl]phenyl}-3-(2-methylphenyl)urea;

1-{4-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea;

3-[3-(2-amino-7,8-dihydropyrido[4,3-d]pyrimidin-6(5H)-yl)-4-methyl-2-oxopyridin-1(2H)-yl]-N-(3-methyl-2-furyl)benzamide;

4-[3-(2-amino-7,8-dihydropyrido[4,3-d]pyrimidin-6(5H)-yl)-4-methyl-2-oxopyridin-1(2H)-yl]-N-(3-methyl-2-furyl)benzamide;

1-{3-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea;

4-[3-(2-amino-7,8-dihydropyrido[4,3-d]pyrimidin-6(5H)-yl)-4-methyl-2-oxopyridin-1(2H)-yl]-N-(2-methylphenyl)benzamide;

4-[({[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]amino}carbonyl)amino]butanoic acid;

2-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)benzamide;

2-hydroxyethyl[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]carbamate;

4-({[(6-{4-methyl-1-[4-({[(3-methyl-2-furyl)methyl]amino}carbonyl)phenyl]-2-oxo-1,2-dihydropyridin-3-yl}-5,6,7,8-tetrahydropyrido[4,3-d]pyrimidin-2-yl)amino]carbonyl}amino)butanoic acid;

4-[({[6-(4-methyl-1-{4-[(2-methyl benzoyl)amino]phenyl}-2-oxo-1,2-dihydropyridin-3-yl)-5,6,7,8-tetrahydropyrido[4,3-d]pyrimidin-2-yl]amino}carbonyl)amino]butanoic acid;

2-hydroxyethyl[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]carbamate;

3-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)-2-furamide;

1-(6-{1-[3-(dimethylamino)phenyl]-4-methyl-2-oxo-1,2-dihydropyridin-3-yl}-5,6,7,8-tetrahydropyrido[4,3-d]pyrimidin-2-yl)-3-(3-morpholin-4-ylpropyl)urea;

2-hydroxyethyl (6-{1-[3-(dimethylamino)phenyl]-4-methyl-2-oxo-1,2-dihydropyridin-3-yl}-5,6,7,8-tetrahydropyrido[4,3-d]pyrimidin-2-yl)carbamate;

4-({[(6-{1-[3-(dimethylamino)phenyl]-4-methyl-2-oxo-1,2-dihydropyridin-3-yl}-5,6,7,8-tetrahydropyrido[4,3-d]pyrimidin-2-yl)amino]carbonyl}amino)butanoic acid;

3-(4-{[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]amino}phenyl)propanoic acid;

N-{4-[3-(2-anilino-7,8-dihydropyrido[4,3-d]pyrimidin-6(5H)-yl)-4-methyl-2-oxopyridin-1(2H)-yl]phenyl}-2-methylbenzamide;

3-{4-[(6-{4-methyl-1-[4-({[(3-methyl-2-furyl)methyl]amino}carbonyl)phenyl]-2-oxo-1,2-dihydropyridin-3-yl}-5,6,7,8-tetrahydropyrido[4,3-d]pyrimidin-2-yl)amino]phenyl}propanoic acid;

4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}-N-[(3-methyl-2-furyl)methyl]benzamide;

4-[3-(2-anilino-7,8-dihydropyrido[4,3-d]pyrimidin-6(5H)-yl)-4-methyl-2-oxopyridin-1(2H)-yl]-N-[(3-methyl-2-furyl)methyl]benzamide;

3-(4-{[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]amino}phenyl)propanoic acid;

N-(4-{3-[2-{[4-(13-hydroxy-5,8,11-trioxa-2-azatridec-1-yl)phenyl]amino}-7,8-dihydropyrido[4,3-d]pyrimidin-6(5H)-yl]-4-methyl-2-oxopyridin-1(2H)-yl}phenyl)-3-methyl-2-furamide;

N-(4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}phenyl)-3-methyl-2-furamide;

N-{4-[3-{2-[(4-{4-[2-(2-hydroxyethoxy)ethyl]piperazin-1-yl}phenyl)amino]-7,8-dihydropyrido[4,3-d]pyrimidin-6(5H)-yl}-4-methyl-2-oxopyridin-1(2H)-yl]phenyl}-3-methyl-2-furamide;

N-{4-[3-(2-anilino-7,8-dihydropyrido[4,3-d]pyrimidin-6(5H)-yl)-4-methyl-2-oxopyridin-1(2H)-yl]phenyl}-3-methyl-2-furamide;

3-{4-[(6-{1-[3-(dimethylamino)phenyl]-4-methyl-2-oxo-1,2-dihydropyridin-3-yl}-5,6,7,8-tetrahydropyrido[4,3-d]pyrimidin-2-yl)amino]phenyl}propanoic acid;

1-[3-(dimethylamino)phenyl]-3-[2-({4-[2-(4-hydroxypiperidin-1-yl)ethyl]phenyl}amino)-7,8-dihydropyrido[4,3-d]pyrimidin-6(5H)-yl]-4-methylpyridin-2(1H)-one;

3-(2-anilino-7,8-dihydropyrido[4,3-d]pyrimidin-6(5H)-yl)-1-[3-(dimethylamino)phenyl]-4-methylpyridin-2(1H)-one;

3-(2-amino-7,8-dihydropyrido[4,3-d]pyrimidin-6(5H)-yl)pyridin-2(1H)-one;

3-(2-amino-7,8-dihydropyrido[4,3-d]pyrimidin-6(5H)-yl)-4-methylpyridin-2(1H)-one.

Compounds of formula I are useful as protein kinase inhibitors. As such, compounds of formula I will be useful for treating diseases related to protein kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, lung carcinomas, breast carcinomas, Non Hodgkin's lymphomas, ovarian carcinoma, pancreatic cancer, malignant pleural mesothelioma, melanoma, arthritis, restenosis, hepatic cirrhosis, atherosclerosis, psoriasis, rosacea, diabetic mellitus, wound healing, inflammation and neurodegenerative diseases and preferably ophthalmic diseases, i.e. diabetic retinopathy, retinopathy of prematurity, macular edema, retinal vein occlusion, exudative or neovascular age-related macular degeneration, high-risk eyes (i.e. fellow eyes have neovascular age-related macular degeneration) with dry age-related macular degeneration, neovascular disease associated with retinal vein occlusion, neovascular disease (including choroidal neovascularization) associated with the following: pathologic myopia, pseudoxanthoma elasticum, optic nerve drusen, traumatic choroidal rupture, atrophic macular degeneration, geographic atrophy, central serous retinopathy, cystoid macular edema, diabetic retinopathy, proliferative diabetic retinopathy, diabetic macular edema, rubeosis iridis, retinopathy of prematurity, Central and branch retinal vein occlusions, inflammatory/infectious retinal, neovascularization/edema, corneal neovascularization, hyperemia related to an actively inflamed pterygia, recurrent pterygia following excisional surgery, post-excision, progressive pterygia approaching the visual axis, prophylactic therapy to prevent recurrent pterygia, of post-excision, progressive pterygia approaching the visual axis, chronic low grade hyperemia associated with pterygia, neovascular glaucoma, iris neovascularization, idiopathic etiologies, presumed ocular histoplasmosis syndrome, retinopathy of prematurity, chronic allergic conjunctivitis, ocular rosacea, blepharoconjunctivitis, recurrent episcleritis, keratoconjunctivitis sicca, ocular graft vs host disease, etc.

Some compounds of Formula I and some of their intermediates may have at least one asymmetric center in their structure. This asymmetric center may be present in an R or S configuration, said R and S notation is used in correspondence with the rules described in Pure Applied Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention is further directed to pharmaceutical compositions comprising a pharmaceutically effective amount of one or more of the above-described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made.

Scheme 1

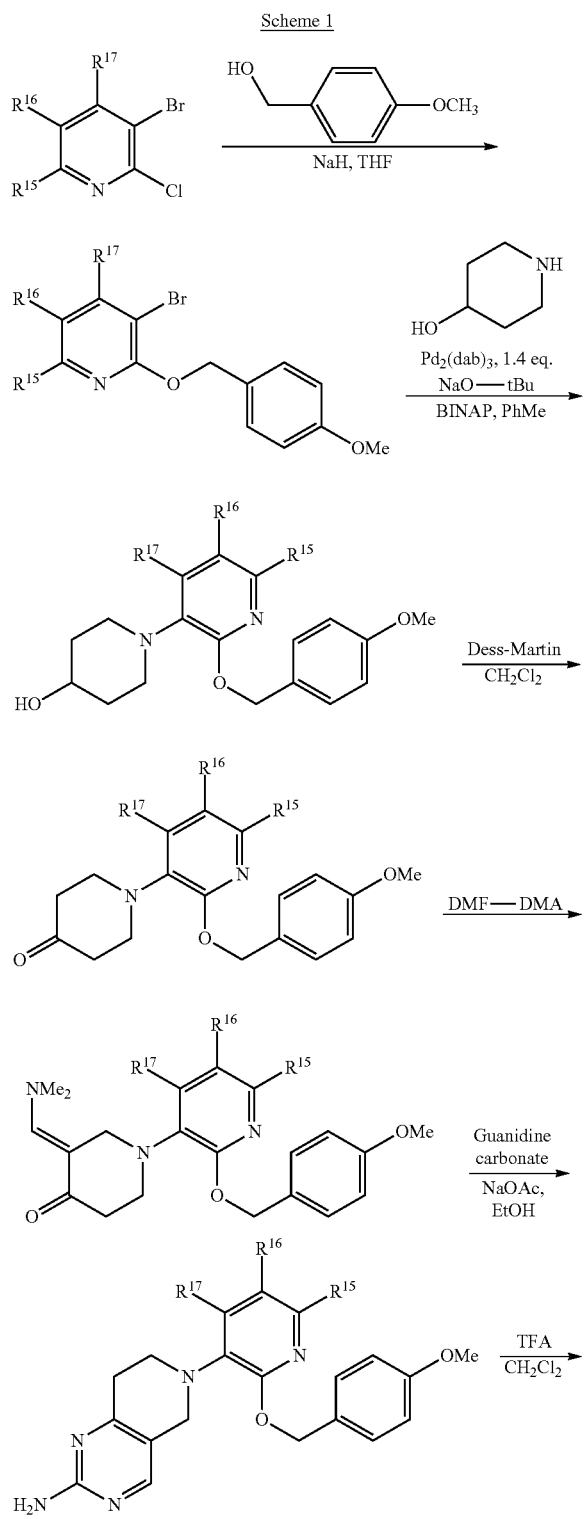

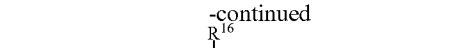

At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

The present invention is not to be limited in scope by the exemplified embodiments which are intended as illustrations of single aspects of the invention only. Indeed, various modifications of the invention in addition to those described herein will become apparent to those skilled in the art from the foregoing description.

DETAILED DESCRIPTION OF THE INVENTION

The present invention relates to a method of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders, which comprises administering a pharmaceutical composition comprising a therapeutically effective amount of at least one kinase inhibitor as described herein.

In another aspect, the invention provides the use of at least one kinase inhibitor for the manufacture of a medicament for the treatment of a disease or a condition mediated by tyrosine kinases in a mammal.

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACDLabs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds is performed according to the following methods; NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

In particular the compounds of the present invention are selected from the compounds of Table 1, below, wherein: $R^{15}$ is hydrogen, $R^{16}$ is hydrogen, $Z^1$ is $(CR^4R^5)_n$, $Z^2$ is $(CR^6R^7)_m$, Y is N, $R^2$ is hydrogen, $R^4$ is hydrogen, $R^5$ is hydrogen, $R^6$ is hydrogen, $R^7$ is hydrogen, n is 2, m is 1, $R^3$ is formula II.

TABLE 1

| Ex. | $R^1$ | $R^{17}$ | $R^{14}$ | | Compound Name |
|---|---|---|---|---|---|
| 2 | NH$_2$ | H | | 4-(tert-butyl)phenyl group | 3-(2-amino-7,8-dihydropyrido[4,3-d]pyrimidin-6(5H)-yl)-1-(4-(tert-butyl)phenyl)pyridin-2(1H)-one |
| 4 | NH$_2$ | CH$_3$ | | 4-(tert-butyl)phenyl group | 3-(2-amino-7,8-dihydropyrido[4,3-d]pyrimidin-6(5H)-yl)-1-(4-(tert-butylphenyl)-4-methylpyridin-2(1H)-one |
| 5 | NH$_2$ | CH$_3$ | | 4-methoxyphenyl group | 3-(2-amino-7,8-dihydropyrido[4,3-d]pyrimidin-6(5H)-yl)-1-(4-methoxyphenyl)-4-methylpyridin-2(1H)-one |
| 6 | NH$_2$ | CH$_3$ | | 4-(2-methoxyethyl)phenyl group | 3-(2-amino-7,8-dihydropyrido[4,3-d]pyrimidin-6(5H)-yl)-1-(4-(2-methoxyethyl)phenyl)-4-methylpyridin-2(1H)-one |
| 7 | NH$_2$ | CH$_3$ | | 3-thienyl group | 3-(2-amino-7,8-dihydropyrido[4,3-d]pyrimidin-6(5H)-yl)-4-methyl-1-(3-thienyl)pyridin-2(1H)-one |

TABLE 1-continued

| Ex. | R¹ | R¹⁷ | R¹⁴ | Compound Name |
|---|---|---|---|---|
| 8 | NH₂ | CH₃ | 1-methyl-1H-pyrazol-3-yl | 3-(2-amino-7,8-dihydropyrido[4,3-d]pyrimidin-6(5H)-yl)-4-methyl-1-(1-methyl-1H-pyrazol-3-yl)-1,6-dihyrdopyridin-2(3H)-one |
| 9 | NH₂ | CH₃ | 3-methylphenyl (m-tolyl) | 3-(2-amino-7,8-dihydropyrido[4,3-d]pyrimidin-6(5H)-yl)-4-methyl-1-(m-toly)-1,6-dihyrdopyridin-2(3H)-one |
| 10 | NH₂ | CH₃ | 4-methylphenyl | 3-(2-amino-7,8-dihydropyrido[4,3-d]pyrimidin-6(5H)-yl)-4-methyl-1-(4-methylphenyl)pyridin-2(1H)-one |
| 11 | NH₂ | CH₃ | 2-methylphenyl | 3-(2-amino-7,8-dihydropyrido[4,3-d]pyrimidin-6(5H)-yl)-4-methyl-1-(2-methylphenyl)pyridin-2(1H)-one |
| 12 | NH₂ | CH₃ | 3-tert-butylphenyl | 3-(2-amino-7,8-dihydropyrido[4,3-d]pyrimidin-6(5H)-yl)-1-(3-tert-butylphenyl)-4-methylpyridin-2(1H)-one |
| 13 | NH₂ | CH₃ | 4-(dimethylamino)phenyl | 3-(2-amino-7,8-dihydropyrido[4,3-d]pyrimidin-6(5H)-yl)-1-[4-(dimethylamino)phenyl]-4-methylpyridin-2(1H)-one |
| 14 | NH₂ | CH₃ | 3-(dimethylamino)phenyl | 3-(2-amino-7,8-dihydropyrido[4,3-d]pyrimidin-6(5H)-yl)-1-[3-(dimethylamino)phenyl]-4-methylpyridin-2(1H)-one |
| 15 | NH₂ | CH₃ | 4-(tert-butoxycarbonylamino)phenyl | tert-butyl {4-[3-(2-amino-7,8-dihydropyrido[4,3-d]pyrimidin-6(5H)-yl)4-methyl-2-oxopyridin-1(2H)-yl]phenyl}carbamate |
| 16 | NH₂ | CH₃ | 4-aminophenyl | 3-(2-amino-7,8-dihydropyrido[4,3-d]pyrimidin-6(5H)-yl)-1-(4-aminophenyl)-4-methylpyridin-2(1H)-one |

TABLE 1-continued

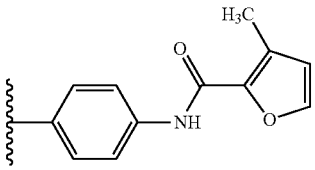

| Ex. | R¹ | R¹⁷ | R¹⁴ | | Compound Name |
|---|---|---|---|---|---|
| 17 | NH₂ | CH₃ | | 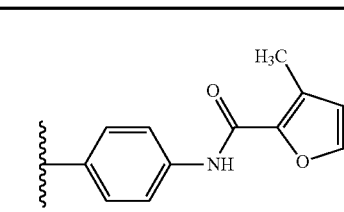 | N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide |
| 18 | NH₂ | CH₃ | | 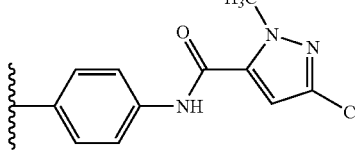 | N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide |
| 19 | NH₂ | CH₃ | | 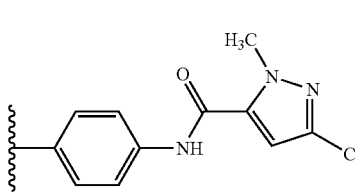 | tert-butyl {4-[3-(2-amino-7,8-dihydropyrido[4,3-d]pyrimidin-6(5H)-yl)-4-methyl-2-oxopyridin-1(2H)-yl]phenyl}carbamate |
| 20 | NH₂ | CH₃ | | 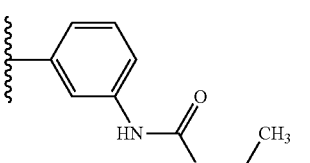 | 3-(2-amino-7,8-dihydropyrido[4,3-d]pyrimidin-6(5H)-yl)-1-(4-aminophenyl)-4-methylpyridin-2(1H)-one |
| 21 | NH₂ | CH₃ | | 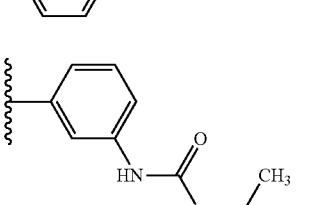 | N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide |
| 22 | NH₂ | CH₃ | | 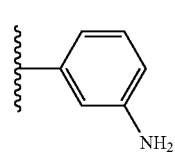 | N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide |

TABLE 1-continued

| Ex. | R¹ | R¹⁷ | R¹⁴ | Compound Name |
|---|---|---|---|---|
| 23 | NH₂ | CH₃ | 4-(2-methylbenzamido)phenyl | N-{4-[3-(2-amino-7,8-dihydropyrido[4,3-d]pyrimidin-6(5H)-yl)-4-methyl-2-oxopyridin-1(2H)-yl]phenyl}-2-methylbenzamide |
| 24 | NH₂ | CH₃ | 4-(4-chlorobenzamido)phenyl | N-{4-[3-(2-amino-7,8-dihydropyrido[4,3-d]pyrimidin-6(5H)-yl)-4-methyl-2-oxopyridin-1(2H)-yl]phenyl}-4-chlorobenzamide |
| 25 | NH₂ | CH₃ | 4-(3-chloro-4-fluorobenzamido)phenyl | N-{4-[3-(2-amino-7,8-dihydropyrido[4,3-d]pyrimidin-6(5H)-yl)-4-methyl-2-oxopyridin-1(2H)-yl]phenyl}-3-chloro-4-fluorobenzamide |
| 26 | NH₂ | CH₃ | 4-[3-(methylthio)benzamido]phenyl | N-{4-[3-(2-amino-7,8-dihydropyrido[4,3-d]pyrimidin-6(5H)-yl)-4-methyl-2-oxopyridin-1(2H)-yl]phenyl}-3-(methylthio)benzamide |
| 27 | NH₂ | CH₃ | 4-[4-chloro-3-(trifluoromethyl)benzamido]phenyl | N-{4-[3-(2-amino-7,8-dihydropyrido[4,3-d]pyrimidin-6(5H)-yl)-4-methyl-2-oxopyridin-1(2H)-yl]phenyl}-4-chloro-3-(trifluoromethyl)benzamide |
| 28 | NH₂ | CH₃ | 4-[3-(trifluoromethyl)benzamido]phenyl | N-{4-[3-(2-amino-7,8-dihydropyrido[4,3-d]pyrimidin-6(5H)-yl)-4-methyl-2-oxopyridin-1(2H)-yl]phenyl}-3-(trifluoromethyl)benzamide |
| 29 | NH₂ | CH₃ | 4-benzamidophenyl | N-{4-[3-(2-amino-7,8-dihydropyrido[4,3-d]pyrimidin-6(5H)-yl)-4-methyl-2-oxopyridin-1(2H)-yl]phenyl}benzamide |

TABLE 1-continued

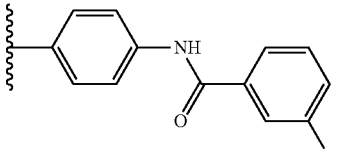

| Ex. | R¹ | R¹⁷ | R¹⁴ | Compound Name |
|-----|-----|------|-----|---------------|
| 30 | NH₂ | CH₃ | 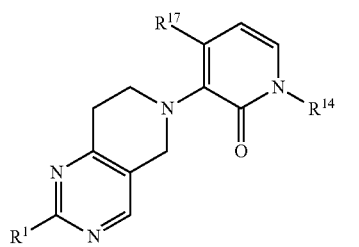 | N-{4-[3-(2-amino-7,8-dihydropyrido[4,3-d]pyrimidin-6(5H)-yl)-4-methyl-2-oxopyridin-1(2H)-yl]phenyl}-3-bromobenzamide |
| 31 | NH₂ | CH₃ | 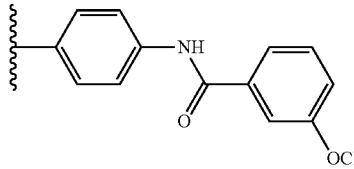 | N-{4-[3-(2-amino-7,8-dihydropyrido[4,3-d]pyrimidin-6(5H)-yl)-4-methyl-2-oxopyridin-1(2H)-yl]phenyl}-3-methoxybenzamide |
| 32 | NH₂ | CH₃ | 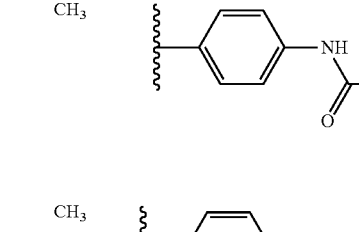 | N-{4-[3-(2-amino-7,8-dihydropyrido[4,3-d]pyrimidin-6(5H)-yl)-4-methyl-2-oxopyridin-1(2H)-yl]phenyl}-3-methylthiophene-2-carboxamide |
| 33 | NH₂ | CH₃ | 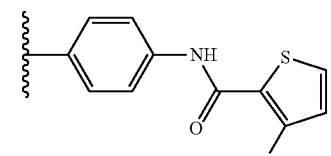 | N-{4-[3-(2-amino-7,8-dihydropyrido[4,3-d]pyrimidin-6(5H)-yl)-4-methyl-2-oxopyridin-1(2H)-yl]phenyl}-3-methylbenzamide |
| 34 | NH₂ | CH₃ | 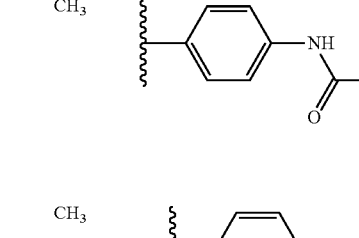 | N-{4-[3-(2-amino-7,8-dihydropyrido[4,3-d]pyrimidin-6(5H)-yl)-4-methyl-2-oxopyridin-1(2H)-yl]phenyl}-4-methylbenzamide |
| 35 | NH₂ | CH₃ | 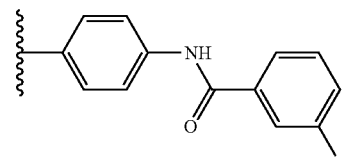 | N-{4-[3-(2-amino-7,8-dihydropyrido[4,3-d]pyrimidin-6(5H)-yl)-4-methyl-2-oxopyridin-1(2H)-yl]phenyl}-3,4-dimethylbenzamide |
| 36 | NH₂ | CH₃ | 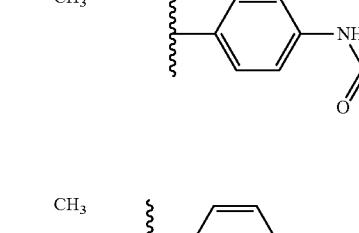 | N-{4-[3-(2-amino-7,8-dihydropyrido[4,3-d]pyrimidin-6(5H)-yl)-4-methyl-2-oxopyridin-1(2H)-yl]phenyl}-3-chloro-4-methoxybenzamide |

TABLE 1-continued

| Ex. | R¹ | R¹⁷ | R¹⁴ | Compound Name |
|---|---|---|---|---|
| 37 | NH₂ | CH₃ | 4-[NH-C(O)-(2-F,5-CF₃-phenyl)]phenyl | N-{4-[3-(2-amino-7,8-dihydropyrido[4,3-d]pyrimidin-6(5H)-yl)-4-methyl-2-oxopyridin-1(2H)-yl]phenyl}-2-fluoro-5-(trifluoromethyl)benzamide |
| 38 | NH₂ | CH₃ | 4-[NH-C(O)-(2-F,5-CH₃-phenyl)]phenyl | N-{4-[3-(2-amino-7,8-dihydropyrido[4,3-d]pyrimidin-6(5H)-yl)-4-methyl-2-oxopyridin-1(2H)-yl]phenyl}-2-fluoro-5-methylbenzamide |
| 39 | NH₂ | CH₃ | 4-[NH-C(O)-(5-tert-butylisoxazol-3-yl)]phenyl | N-{4-[3-(2-amino-7,8-dihydropyrido[4,3-d]pyrimidin-6(5H)-yl)-4-methyl-2-oxopyridin-1(2H)-yl]phenyl}-5-tert-butylisoxazole-3-carboxamide |
| 40 | NH₂ | CH₃ | 4-[NH-C(O)-(3-CF₃,4-OCH₃-phenyl)]phenyl | N-{4-[3-(2-amino-7,8-dihydropyrido[4,3-d]pyrimidin-6(5H)-yl)-4-methyl-2-oxopyridin-1(2H)-yl]phenyl}-4-methoxy-3-(trifluoromethyl)benzamide |
| 41 | NH₂ | CH₃ | 4-[NH-C(O)-(3-SOCH₃-phenyl)]phenyl | N-{4-[3-(2-amino-7,8-dihydropyrido[4,3-d]pyrimidin-6(5H)-yl)-4-methyl-2-oxopyridin-1(2H)-yl]phenyl}-3-(methylsulfinyl)benzamide |
| 42 | NH₂ | CH₃ | 4-[NH-C(O)-(3-COOH-phenyl)]phenyl | 3-[({4-[3-(2-amino-7,8-dihydropyrido[4,3-d]pyrimidin-6(5H)-yl)-4-methyl-2-oxopyridin-1(2H)-yl]phenyl}amino)carbonyl]benzoic acid |
| 43 | NH₂ | CH₃ | 4-[NH-C(O)-(4-CH₂CH₂COOH-phenyl)]phenyl | 3-{4-[({4-[3-(2-amino-7,8-dihydropyrido[4,3-d]pyrimidin-6(5H)-yl)-4-methyl-2-oxopyridin-1(2H)-yl]phenyl}amino)carbonyl]phenyl}propanoic acid |
| 44 | NH₂ | CH₃ | 4-[NH-C(O)-(3-CF₃,4-(4-methylpiperazin-1-ylmethyl)-phenyl)]phenyl | N-{4-[3-(2-amino-7,8-dihydropyrido[4,3-d]pyrimidin-6(5H)-yl)-4-methyl-2-oxopyridin-1(2H)-yl]phenyl}-4-[(4-methylpiperazin-1-yl)methyl]-3-(trifluoromethyl)benzamide |

TABLE 1-continued

| Ex. | R¹ | R¹⁷ | R¹⁴ | Compound Name |
|---|---|---|---|---|
| 45 | NH₂ | CH₃ | 4-fluorophenyl-C(O)-NH-(4-phenyl) | N-{4-[3-(2-amino-7,8-dihydropyrido[4,3-d]pyrimidin-6(5H)-yl)-4-methyl-2-oxopyridin-1(2H)-yl]phenyl}-4-fluorobenzamide |
| 46 | NH₂ | CH₃ | 3,4-dimethoxyphenyl-C(O)-NH-(4-phenyl) | N-{4-[3-(2-amino-7,8-dihydropyrido[4,3-d]pyrimidin-6(5H)-yl)-4-methyl-2-oxopyridin-1(2H)-yl]phenyl}-3,4-dimethoxybenzamide |
| 47 | NH₂ | CH₃ | 2-furyl-C(O)-NH-(4-phenyl) | N-{4-[3-(2-amino-7,8-dihydropyrido[4,3-d]pyrimidin-6(5H)-yl)-4-methyl-2-oxopyridin-1(2H)-yl]phenyl}-2-furamide |
| 48 | NH₂ | CH₃ | 5-methyl-2-furyl-C(O)-NH-(4-phenyl) | N-{4-[3-(2-amino-7,8-dihydropyrido[4,3-d]pyrimidin-6(5H)-yl)-4-methyl-2-oxopyridin-1(2H)-yl]phenyl}-5-methyl-2-furamide |
| 49 | NH₂ | CH₃ | 4-phenyl-C(O)-N[(3-methyl-2-furyl)methyl] | 4-[3-(2-amino-7,8-dihydropyrido[4,3-d]pyrimidin-6(5H)-yl)-4-methyl-2-oxopyridin-1(2H)-yl]-N-[(3-methyl-2-furyl)methyl]benzamide |
| 50 | NH₂ | CH₃ | (2-methylphenyl)-NH-C(O)-NH-(4-phenyl) | 1-{4-[3-(2-amino-7,8-dihydropyrido[4,3-d]pyrimidin-6(5H)-yl)-4-methyl-2-oxopyridin-1(2H)-yl]phenyl}-3-(2-methylphenyl)urea |
| 51 | NH₂ | CH₃ | (3-methyl-2-furyl)-NH-C(O)-NH-(4-phenyl) | 1-{4-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea |

TABLE 1-continued

| Ex. | R¹ | R¹⁷ | R¹⁴ | Compound Name |
|---|---|---|---|---|
| 52 | NH₂ | CH₃ | (3-benzamido group with N-(3-methyl-2-furyl)) | 3-[3-(2-amino-7,8-dihydropyrido[4,3-d]pyrimidin-6(5H)-yl)-4-methyl-2-oxopyridin-1(2H)-yl]-N-(3-methyl-2-furyl)benzamide |
| 53 | NH₂ | CH₃ | (4-benzamido group with N-(3-methyl-2-furyl)) | 4-[3-(2-amino-7,8-dihydropyrido[4,3-d]pyrimidin-6(5H)-yl)-4-methyl-2-oxopyridin-1(2H)-yl]-N-(3-methyl-2-furyl)benzamide |
| 54 | NH₂ | CH₃ | (3-phenylurea with 3-methyl-2-furyl) | 1-{3-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea |
| 55 | NH₂ | CH₃ | (4-benzamido group with N-(2-methylphenyl)) | 4-[3-(2-amino-7,8-dihydropyrido[4,3-d]pyrimidin-6(5H)-yl)-4-methyl-2-oxopyridin-1(2H)-yl]-N-(2-methylphenyl)benzamide |
| 56 | -NH-C(O)-NH-(CH₂)₄-COOH | CH₃ | (4-phenyl with NH-C(O)-furyl-CH₃) | 4-[({6-(4-methyl-1-{[(3-methyl-2-furoyl)amino]phneyl}-2-oxo-1,2-dihydropyridin-3-yl)-5,6,7,8-tetrahydropyrido[4,3-d]pyrimidin-2-yl]amino}carbonyl)amino]butanoic acid |
| 57 | -NH-C(O)-NH-(CH₂)₃-morpholine | CH₃ | (4-phenyl with NH-C(O)-2-methylphenyl) | 2-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)benzamide |
| 58 | -NH-C(O)-O-CH₂CH₂OH | CH₃ | (4-phenyl with NH-C(O)-2-methylphenyl) | 2-hydroxyethyl [6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]carbamate |

TABLE 1-continued

| Ex. | R¹ | R¹⁷ | R¹⁴ | Compound Name |
|---|---|---|---|---|
| 59 | (urea linked to -(CH₂)₃-COOH) | CH₃ | 4-[(3-methyl-2-furyl)methylamino]carbonyl-phenyl with 3-methylfuran-2-carboxamide | 4-({[(6-{4-methyl-1-[4-({[(3-methyl-2-furyl)methyl]amino}carbonyl)phenyl]-2-oxo-1,2-dihydropyridin-3-yl}-5,6,7,8-tetrahydropyrido[4,3-d]pyrimidin-2-yl)amino]carbonyl}amino)butanoic acid |
| 60 | (urea linked to -(CH₂)₄-COOH) | CH₃ | 4-[(2-methylbenzoyl)amino]phenyl with 2-methylbenzamide | 4-({[(6-{4-methyl-1-{4-[(2-methylbenzoyl)amino]phenyl}-2-oxo-1,2-dihydropyridin-3-yl}-5,6,7,8-tetrahydropyrido[4,3-d]pyrimidin-2-yl)amino]carbonyl)amino]butanoic acid |
| 61 | (carbamate linked to -CH₂CH₂OH) | CH₃ | 4-[(3-methyl-2-furoyl)amino]phenyl | 2-hydroxyethyl [6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]carbamate |
| 62 | (urea linked to -(CH₂)₃-morpholine) | CH₃ | 4-({[(3-morpholin-4-ylpropyl)amino]carbonyl}amino)phenyl with 3-methylfuran-2-carboxamide | 3-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)-2-furamide |
| 63 | (urea linked to -(CH₂)₃-morpholine) | CH₃ | 3-(dimethylamino)phenyl | 1-(6-{1-[3-(dimethylamino)phenyl]-4-methyl-2-oxo-1,2-dihydropyridin-3-yl}-5,6,7,8-tetrahydropyrido[4,3-d]pyrimidin-2-yl)-3-(3-morpholin-4-ylpropyl)urea |
| 64 | (carbamate linked to -CH₂CH₂OH) | CH₃ | 3-(dimethylamino)phenyl | 2-hydroxyethyl (6-{1-[3-(dimethylamino)phenyl]-4-methyl-2-oxo-1,2-dihydropyridin-3-yl}-5,6,7,8-tetrahydropyrido[4,3-d]pyrimidin-2-yl)carbamate |

TABLE 1-continued

| Ex. | R¹ | R¹⁷ | R¹⁴ | Compound Name |
|---|---|---|---|---|
| 65 | (tert-butyl urea linked to pentanoic acid COOH) | CH₃ | (3-dimethylamino phenyl) | 4-({[(6-{1-[3-(dimethylamino)phenyl]-4-methyl-2-oxo-1,2-dihydropyridin-3-yl)-5,6,7,8-tetrahydropyrido[4,3-d]pyrimidin-2-yl]amino]carbonyl)amino)b |
| 66 | (HN-phenyl-CH₂CH₂COOH, para) | CH₃ | (phenyl-NH-C(O)-2-methylphenyl) | 3-(4-{[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]amino}phenyl)propanoic acid |
| 67 | (HN-phenyl) | CH₃ | (phenyl-NH-C(O)-2-methylphenyl) | N-{4-[3-(2-anilino-7,8-dihydropyrido[4,3-d]pyrimidin-6(5H)-yl)-4-methyl-2-oxopyridin-1(2H)-yl]phenyl}-2-methylbenzamide |
| 68 | (HN-phenyl-CH₂CH₂COOH, para) | CH₃ | (phenyl-C(O)NH-CH₂-(3-methyl-2-furyl)) | 3-{4-[(6-{4-methyl-1-[4-({[(3-methyl-2-furyl)methyl]amino}carbonyl)phenyl]-2-oxo-1,2-dihydropyridin-3-yl)-5,6,7,8-tetrahydropyrido[4,3-d]pyrimidin-2-yl]amino]phenyl}propanoic acid |
| 69 | (phenyl-CH₂CH₂-N(4-hydroxypiperidin-1-yl)) | CH₃ | (phenyl-C(O)NH-CH₂-(3-methyl-2-furyl)) | 4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}-N-[(3-methyl-2-furyl)methyl]benzamide |
| 70 | (HN-phenyl) | CH₃ | (phenyl-C(O)NH-CH₂-(3-methyl-2-furyl)) | 4-[3-(2-anilino-7,8-dihydropyrido[4,3-d]pyrimidin-6(5H)-yl)-4-methyl-2-oxopyridin-1(2H)-yl]-N-[(3-methyl-2-furyl)methyl]benzamide |

TABLE 1-continued

| Ex. | R¹ | R¹⁷ | R¹⁴ | Compound Name |
|---|---|---|---|---|
| 71 | 4-(2-carboxyethyl)phenyl | CH₃ | 4-[(3-methyl-2-furoyl)amino]phenyl | 3-(4-{[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]amino}phenyl) propanoic acid |
| 72 | 4-{[(2-{2-[2-(2-hydroxyethoxy)ethoxy]ethoxy}ethyl)amino]methyl}anilino | CH₃ | 4-[(3-methyl-2-furoyl)amino]phenyl | N-(4-{3-[2-{[4-(13-hydroxy-5,8,11-trioxa-2-azatridec-1-yl)phenyl]amino}-7,8-dihydropyrido[4,3-d]pyrimidin-6(5H)-yl]-4-methyl-2-oxopyridin-1(2H)-yl}phenyl)-3-methyl-2-furamide |
| 73 | 4-{2-[4-hydroxypiperidin-1-yl]ethyl}anilino | CH₃ | 4-[(3-methyl-2-furoyl)amino]phenyl | N-(4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}phenyl)-3-methyl-2-furamide |
| 74 | 4-{4-[2-(2-hydroxyethoxy)ethyl]piperazin-1-yl}anilino | CH₃ | 4-[(3-methyl-2-furoyl)amino]phenyl | N-{4-[3-{2-[(4-{4-[2-(2-hydroxyethoxy)ethyl]piperazin-1-yl}phenyl)amino]-7,8-dihydropyrido[4,3-d]pyrimidin-6(5H)-yl}-4-methyl-2-oxopyridin-1(2H)-yl]phenyl}-3-methyl-2-furamide |
| 75 | anilino | CH₃ | 4-[(3-methyl-2-furoyl)amino]phenyl | N-{4-[3-(2-anilino-7,8-dihydropyrido[4,3-d]pyrimidin-6(5H)-yl)-4-methyl-2-oxopyridin-1(2H)-yl]phenyl}-3-methyl-2-furamide |
| 76 | 4-(2-carboxyethyl)anilino | CH₃ | 3-(dimethylamino)phenyl | 3-{4-[(6-{1-[3-(dimethylamino)phenyl]-4-methyl-2-oxo-1,2-dihydropyridin-3-yl}-5,6,7,8-tetrahydropyrido[4,3-d]pyrimidin-2-yl)amino]phenyl} propanoic acid |

TABLE 1-continued

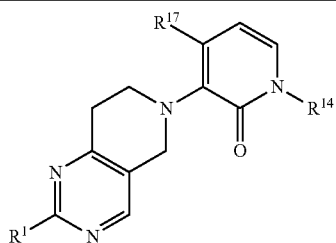

| Ex. | R¹ | R¹⁷ | R¹⁴ | Compound Name |
|---|---|---|---|---|
| 77 | (structure: HN-phenyl-CH₂CH₂-N-piperidine-OH) | CH₃ | (structure: 3-(N,N-dimethylamino)phenyl) | 1-[3-(dimethyl amino)phenyl]-3-[2-({4-[2-(4-hydoxypiperidin-1-yl)ethyl]phenyl}amino)-7,8-dihydropyrido[4,3-d]pyrimidin-6(5H)-yl]-4-methylpyridin-2(1H)-one |
| 78 | (structure: HN-phenyl) | CH₃ | (structure: 3-(N,N-dimethylamino)phenyl) | 3-(2-anilino-7,8-dihydropyrido[4,3-d]pyrimidin-6(5H)-yl)-1-[3-(dimethylamino)phenyl]-4-methylpyridin-2(1H)-one |

Preparation 1

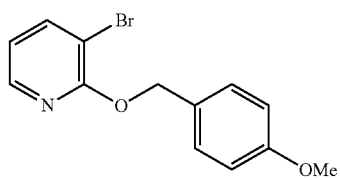 [SMILES: COc1ccc(COc2ncccc2Br)cc1]

3-bromo-2-(4-methoxybenzyloxy)pyridine 3-bromo-2-(4-methoxybenzyloxy)pyridine was prepared by the procedure described in *J. Med. Chem.*, 2008, 51, 3065. A pressure vessel was charged with anhydrous THF (25 ml) and sodium hydride (1.44 g, 36.18 mmol, 60% dispersion). To this stirred mixture was added portionwise a solution of 4-methoxybenzyl alcohol (5.0 g, 36.18 mmol) in anhydrous THF (15 ml). After addition was complete, the mixture was stirred at room temperature for 30 minutes and a solution of 3-bromo-2-chloropyridine (4.64 g, 24.08 mmol) in anhydrous THF (15 ml) was added. The vessel was sealed and the reaction mixture was heated at 75° C. for 6 hours. Upon cooling to room temperature, the reaction mixture was partitioned between ethyl acetate and water. The separated organic layer was washed with water, sat'd NaCl$_{(aq.)}$, dried over MgSO₄, filtered, and concentrated. Elution through a flash column (silica gel 60, 230-400 mesh, 4:1 hexanes: EtOAc) gave the title compound as a clear oil (6.51 g, 92%).

Preparation 2

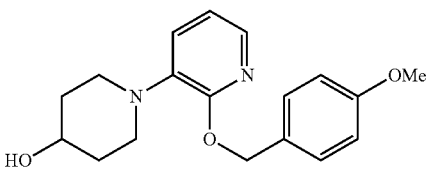 [SMILES: COc1ccc(COc2ncccc2N2CCC(O)CC2)cc1]

2'-(4-Methoxybenzyloxy)-3,4,5,6-tetrahydro-2H-[1,3']bipyridinyl-4-ol

A mixture of 3-bromo-2-(4-methoxybenzyloxy)pyridine (7.25 g, 24.65 mmol), 4-hydroxypiperidine (3.74 g, 36.97 mmol), tris(dibenzylideneacetone)dipalladium (451 mg, 0.493 mmol), racemic-2,2'-bis(diphenylphosphino)-1,1'-binaphthyl (614 mg, 0.986 mmol), and sodium-t-butoxide (3.32 g, 34.51 mmol) in anhydrous toluene (90 ml) was heated at 85° C. under nitrogen for 22 hours. The reaction mixture was diluted with ethyl acetate, washed with sat'd NaCl$_{(aq.)}$, dried (MgSO₄), filtered, and concentrated. Elution through a flash column (silica gel 60, 230-400 mesh, 1:1 hexanes: EtOAc to 3:7 hexanes: EtOAc) gave the title compound as a brown, viscous oil (4.45 g, 57%).

Preparation 3

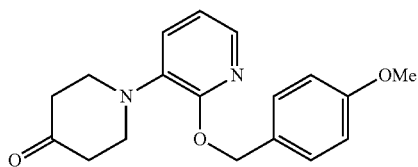 [SMILES: COc1ccc(COc2ncccc2N2CCC(=O)CC2)cc1]

2'-(4-Methoxybenzyloxy)-2,3,5,6-tetrahydro[1,3']bipyridinyl-4-one

A stirred solution of Dess-Martin periodinane (9.19 g, 21.67 mmol) in dichloromethane (95 ml) at room temperature was treated with a solution of 2'-(4-Methoxybenzyloxy)-3,4,5,6-tetrahydro-2H-[1,3']bipyridinyl-4-ol (5.68 g, 18.06 mmol) in dichloromethane (60 ml) and the reaction mixture was stirred at room temperature (a mild exotherm was observed). After 1 hour, the reaction mixture was washed with sat'd $Na_2S_2O_{3(aq.)}$, sat'd $NaHCO_{3(aq.)}$, sat'd $NaCl_{(aq.)}$, dried over $MgSO_4$, filtered, and concentrated. Elution through a flash column (silica gel 60, 230-400 mesh, 7:3 hexanes:EtOAc to 3:2 hexanes:EtOAc) gave the title compound as a yellow, viscous oil (4.01 g, 71%).

Preparation 4

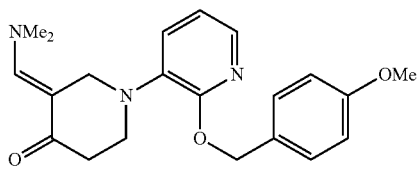 [SMILES: COc1ccc(COc2ncccc2N2CCC(=O)/C(=C/N(C)C)C2)cc1]

3-Dimethylaminomethylene-2'-(4-methoxybenzyloxy)-2,3,5,6-tetrahydro[1,3']bipyridinyl-4-one A solution of 2'-(4-methoxybenzyloxy)-2,3,5,6-tetrahydro[1,3']bipyridinyl-4-one (962 mg, 3.08 mmol) in N,N-dimethylformamide-dimethylacetal (7.0 ml, 52.28 mmol) was heated at 75° C. for 21 hours. The solvent was removed in vacuo and the residue was eluted through a flash column (silica gel 60, 230-400 mesh, 8% methanol in EtOAc) to give the title compound as an orange, viscous oil (628 mg, 56%).

Preparation 5

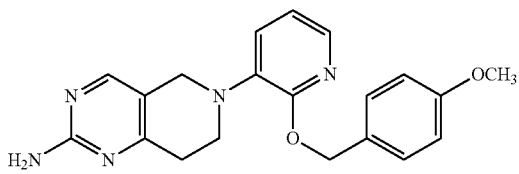 [SMILES: COc1ccc(COc2ncccc2N2CCc3nc(N)ncc3C2)cc1]

6-{2-[(4-methoxybenzyl)oxy]pyridin-3-yl}-5,6,7,8-tetrahydropyrido[4,3-d]pyrimidin-2-amine A solution of 3-dimethylaminomethylene-2'-(4-methoxybenzyloxy)-2,3,5,6-tetrahydro[1,3']bipyridinyl-4-one (673 mg, 1.83 mmol) in ethanol (100 ml) was treated with guanidine carbonate (1.32 g, 7.33 mmol), followed by addition of sodium acetate trihydrate (1.99 g, 14.64 mmol) and the reaction mixture was refluxed for 21 hours. The solvent was removed in vacuo and the residue was partitioned between water and ethyl acetate. The separated organic layer was dried ($MgSO_4$), filtered, and concentrated. Elution through a flash column (silica gel 60, 230-400 mesh, 6% methanol in EtOAc) gave the title compound as a light yellow, amorphous solid (477 mg, 72%).

Example 1

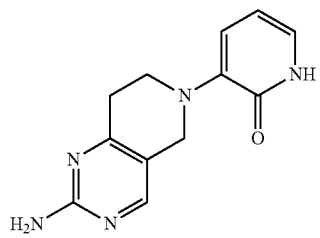 [SMILES: Nc1ncc2c(n1)CCN(c1ccc[nH]c1=O)C2]

3-(2-amino-7,8-dihydropyrido[4,3-d]pyrimidin-6(5H)-yl)pyridin-2(1H)-one

A solution of 6-{2-[(4-methoxybenzyl)oxy]pyridin-3-yl}-5,6,7,8-tetrahydropyrido[4,3-d]pyrimidin-2-amine (1.77 g, 4.87 mmol) in dichloromethane (70 ml) was treated with trifluoroacetic acid (2.68 ml, 36.04 mmol) at room temperature. After stirring for 30 minutes, the solvent and excess acid was removed in vacuo and the residue was treated with ethyl acetate. Washing with sat'd $NaHCO_{3(aq.)}$ gave a yellow, amorphous precipitate. The solid was collected, washed with water, EtOAc, MeOH and dried (774 mg, 65%). The product was suspended in a 2:1 (v/v) mixture of water: MeOH (125 ml) and heated to boiling with vigorous stirring for 1.5 hours. The undissolved solid remaining was collected by filtration while the mixture was still hot and washed with water, MeOH, and dried to give the title compound (478 mg, 40%).

Example 2

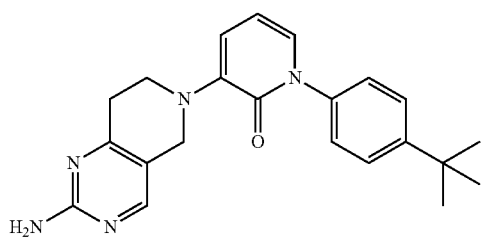 [SMILES: CC(C)(C)c1ccc(-n2cccc(N3CCc4nc(N)ncc4C3)c2=O)cc1]

3-(2-amino-7,8-dihydropyrido[4,3-d]pyrimidin-6(5H)-yl)-1-(4-(tert-butyl)phenyl)pyridin-2(1H)-one)

A mixture of 3-(2-amino-7,8-dihydropyrido[4,3-d]pyrimidin-6(5H)-yl)pyridin-2(1H)-one (52 mg, 0.20 mmol), 1-tert-butyl-4-iodobenzene (0.071 mL, 0.40 mmol), N,N'-dimethylethylenediamine (0.022 mL, 0.20 mmol), potassium phosphate tribasic (170 mg, 0.80 mmol), copper (I) iodide (15 mg, 0.080 mmol) in 1.0 mL NMP was heated at 80° C. for 6 hours. The reaction mixture was partitioned between EtOAc and aqueous NaHCO₃ solution, the EtOAc layer washed with H₂O, brine, dried with anhydrous Na₂SO₄ and rotary evaporated. The resulting oil was chromatographed eluting with CHCl₃, then CHCl₃/EtOAc (1:1), and then 5% MeOH in CHCl₃/EtOAc (1:1). The solid obtained was then triturated with an EtOAc/hexane mixture to give a pale greenish-beige solid (46 mg, 61%). ¹H NMR (DMSO) δ: 8.03 (s, 1H), 7.48-7.54 (m, 2H), 7.28-7.33 (m, 2H), 7.27 (dd, J=6.7, 1.8 Hz, 1H), 6.87 (dd, J=7.3, 1.8 Hz, 1H), 6.37 (s, 2H), 6.27 (t, J=7.0 Hz, 1H), 4.07 (s, 2H), 3.46 (t, J=6.0 Hz, 2H), 2.69 (t, J=5.9 Hz, 2H), 1.33 (s, 9H).

Preparation 7

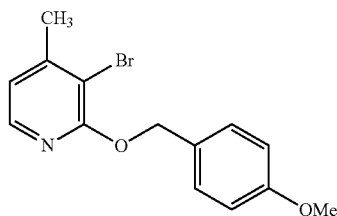 [SMILES: COc1ccc(COc2nccc(C)c2Br)cc1]

3-Bromo-2-(4-methoxybenzyloxy)-4-methylpyridine 3-bromo-2-(4-methoxybenzyloxy)-4-methylpyridine was prepared by the procedure described in J. Med. Chem., 2008, 51, 3065. A pressure vessel was charged with anhydrous THF (25 ml) and sodium hydride (1.44 g, 36.18 mmol, 60% dispersion). To this stirred mixture was added portionwise a solution of 4-methoxybenzyl alcohol (5.0 g, 36.18 mmol) in anhydrous THF (15 ml). After addition was complete, the mixture was stirred at room temperature for 30 minutes and a solution of 3-bromo-2-chloro-4-picoline (4.97 g, 24.08 mmol) in anhydrous THF (15 ml) was added. The vessel was sealed and the reaction mixture was heated at 75° C. for 6 hours. Upon cooling to room temperature, the reaction mixture was partitioned between ethyl acetate and water. The separated organic layer was washed with water, sat'd NaCl$_{(aq.)}$, dried over MgSO₄, filtered, and concentrated. Elution through a flash column (silica gel 60, 230-400 mesh, 4:1 hexanes: EtOAc) gave the title compound as a clear oil which crystallized on standing (6.71 g, 90%).

Preparation 8

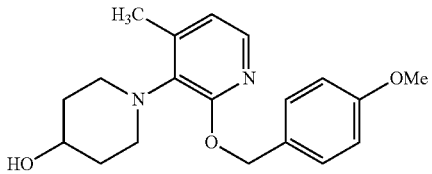 [SMILES: COc1ccc(COc2nccc(C)c2N2CCC(O)CC2)cc1]

2'-(4-Methoxybenzyloxy)-4'-methyl-3,4,5,6-tetrahydro-2H-[1,3']bipyridinyl-4-ol

A mixture of 3-bromo-2-(4-methoxybenzyloxy)-4-methylpyridine (6.40 g, 20.77 mmol), 4-hydroxypiperidine (3.15 g, 31.15 mmol), tris(dibenzylideneacetone)dipalladium (761 mg, 0.831 mmol), racemic-2,2'-bis(diphenylphosphino)-1,1'-binaphthyl (1.03 g, 1.66 mmol), and sodium-t-butoxide (2.79 g, 29.08 mmol) in anhydrous toluene (200 ml) was heated at reflux under nitrogen for 22 hours. Upon cooling to room temperature, the reaction mixture was filtered through celite and the filtrate was diluted with ethyl acetate, washed with sat'd NaCl$_{(aq.)}$, dried (MgSO₄), filtered, and concentrated. Elution through a flash column (silica gel 60, 230-400 mesh, 1:1 hexanes: EtOAc) gave the title compound as a black, viscous oil (4.76 g, 70%).

Preparation 9

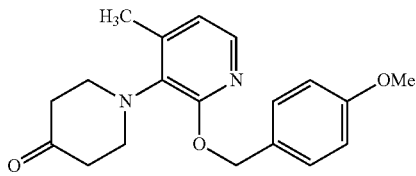 [SMILES: COc1ccc(COc2nccc(C)c2N2CCC(=O)CC2)cc1]

2'-(4-Methoxybenzyloxy)-4'-methyl-2,3,5,6-tetrahydro[1,3']bipyridinyl-4-one

A stirred solution of Dess-Martin periodinane (11.61 g, 27.37 mmol) in dichloromethane (122 ml) at room temperature was treated with a solution of 2'-(4-Methoxybenzyloxy)-4'-methyl-3,4,5,6-tetrahydro-2H-[1,3']bipyridinyl-4-ol (7.49 g, 22.81 mmol) in dichloromethane (81 ml) and the reaction mixture was stirred at room temperature. After 1 hour, the reaction mixture was washed with sat'd Na₂S₂O₃$_{(aq.)}$, sat'd NaHCO₃$_{(aq.)}$, and sat'd NaCl$_{(aq.)}$, dried over MgSO₄, filtered, and concentrated. Elution through a flash column (silica gel 60, 230-400 mesh, 3:2 hexanes:EtOAc) gave the title compound as an off-white, crystalline solid (6.40 g, 86%).

Preparation 10

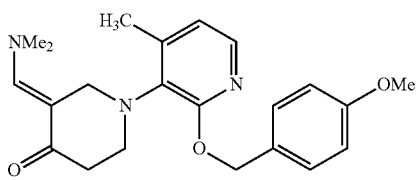 [SMILES: COc1ccc(COc2nccc(C)c2N2CCC(=O)/C(=C/N(C)C)C2)cc1]

3-Dimethylaminomethylene-2'-(4-methoxybenzyloxy)-4'-methyl-2,3,5,6-tetrahydro[1,3']bipyridinyl-4-one A mixture of 2'-(4-Methoxybenzyloxy)-4'-methyl-2,3,5,6-tetrahydro[1,3']bipyridinyl-4-one (6.40 g, 19.61 mmol) in N,N-dimethylformamide-dimethylacetal (44.63 ml, 333.37 mmol) from a freshly opened bottle was heated at 100° C. for 48 hours. The solvent was removed in vacuo and the residue was eluted through a flash column (silica gel 60, 230-400 mesh, EtOAc to 8% methanol in EtOAc) to give title compound as an orange, viscous oil which slowly solidified on standing (5.21 g, 70%).

Preparation 11

6-{2-[(4-methoxybenzyl)oxy]-4-methylpyridin-3-yl}-5,6,7,8-tetrahydropyrido[4,3-d]pyrimidin-2-amine A solution of 3-dimethylaminomethylene-2'-(4-methoxybenzyloxy)-4'-methyl-2,3,5,6-tetrahydro[1,3']bipyridinyl-4-one (5.21 g, 13.66 mmol) in methanol (340 ml) was treated with guanidine carbonate (9.84 g, 54.63 mmol), followed by addition of sodium acetate trihydrate (14.87 g, 109.28 mmol) and the reaction mixture was refluxed for 3 hours. The solvent was removed in vacuo and the residue was partitioned between water and dichloromethane. The separated organic layer was dried (MgSO$_4$), filtered, and concentrated to a red oil. The oil was taken up in a minimal volume of EtOAc and allowed to stand overnight at room temperature. The resulting yellow, crystalline solid was collected, washed with EtOAc, and dried to give the title compound (1.91 g). The mother liquor was concentrated and the residue was eluted through a flash column (silica gel 60, 230-400 mesh, EtOAc) to obtain an additional lot of the title compound (1.05 g) The total amount 2.96 g, 57%). HPLC analysis showed the compound has a purity of 98%.

Example 3

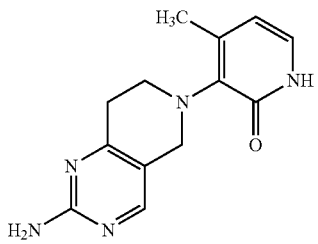 [SMILES: Cc1cc[nH]c(=O)c1N1CCc2nc(N)ncc2C1]

3-(2-amino-7,8-dihydropyrido[4,3-d]pyrimidin-6(5H)-yl)-4-methylpyridin-2(1H)-one A solution of 6-{2-[(4-methoxybenzyl)oxy]-4-methylpyridin-3-yl}-5,6,7,8-tetrahydropyrido[4,3-d]pyrimidin-2-amine (3.92 g, 10.39 mmol) in dichloromethane (150 ml) was treated with trifluoroacetic acid (5.71 ml, 76.89 mmol) at room temperature. After stirring for 30 minutes, the solvent and excess acid was removed in vacuo and the residue was treated with ethyl acetate. Washing with sat'd NaHCO$_{3(aq.)}$ gave a yellow, amorphous precipitate. The solid was collected, washed with water, EtOAc, and dried in vacuo at 50° C. to give (1.65 g, 62%). HPLC analysis showed the compound has a purity of 97%.

Example 4

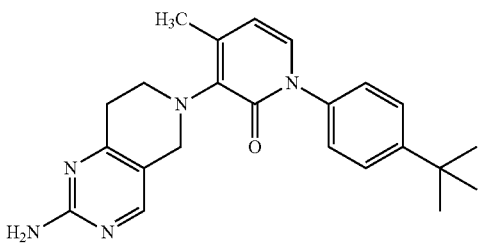 [SMILES: Cc1ccn(-c2ccc(C(C)(C)C)cc2)c(=O)c1N1CCc2nc(N)ncc2C1]

3-(2-amino-7,8-dihydropyrido[4,3-d]pyrimidin-6(5H)-yl)-1-(4-tert-butylphenyl)-4-methylpyridin-2(1H)-one A mixture of 3-(2-amino-7,8-dihydropyrido[4,3-d]pyrimidin-6(5H)-yl)-4-methylpyridin-2(1H)-one, 1-tert-butyl-4-iodobenzene (0.071 mL, 0.40 mmol), N,N'-dimethylethylenediamine (0.022 mL, 0.20 mmol), potassium phosphate tribasic (170 mg, 0.80 mmol), copper (I) iodide (15 mg, 0.080 mmol) in 1.0 mL NMP was heated at 70° C. for 17 hours. The reaction mixture was partitioned between EtOAc and aqueous NaHCO$_3$ solution, the EtOAc layer washed with H$_2$O, brine, dried with anhydrous Na$_2$SO$_4$ and rotary evaporated. The resulting oil was chromatographed eluting with CHCl$_3$, then CHCl$_3$/EtOAc (1:1), and then gradient 3% to 6% MeOH in CHCl$_3$/EtOAc (1:1). The solid obtained was then precipitated from an EtOAc/hexane mixture to give a pale yellow solid (44 mg, 57%). $^1$H NMR (DMSO) δ: 7.94 (s, 1H), 7.48-7.53 (m, 2H), 7.43 (d, J=6.7 Hz, 1H), 7.27-7.33 (m, 2H), 6.30 (s, 2H), 6.19 (d, J=7.0 Hz, 1H), 3.98 (br. s, 2H), 3.31 (br. s, 2H), 2.68 (t, J=5.3 Hz, 2H), 2.19 (s, 3H), 1.32 (s, 9H)

Example 5

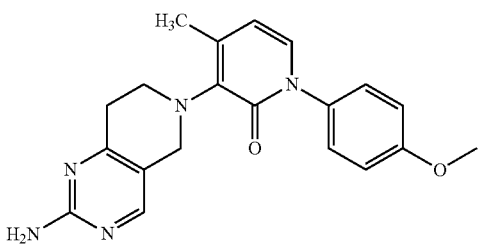 [SMILES: COc1ccc(-n2ccc(C)c(N3CCc4nc(N)ncc4C3)c2=O)cc1]

3-(2-amino-7,8-dihydropyrido[4,3-d]pyrimidin-6(5H)-yl)-1-(4-methoxyphenyl)-4-methylpyridin-2(1H)-one A degassed solution of 3-(2-amino-7,8-dihydropyrido[4,3-d]pyrimidin-6(5H)-yl)-4-methylpyridin-2(1H)-one (25 mg, 0.097 mmol), 4-methoxy-iodobenzene (23 mg, 97 mmol) N1,N2-dimethylethane-1,2-diamine (5 mg, 0.049 mmol), copper iodide (5 mg, 22 mmol), and potassium phosphate (41 mg, 0.194 mmol) in 2 mL of N-methylpyrrolidone was heated to 70° C. After allowing the reaction to stir overnight (19 h) at 70° C., the reaction was complete and allowed to cool to room temperature. The reaction was extracted with EtOAc (3×5 mL) and NaHCO₃ (2×10 mL). The crude organic layers were combined, dried over anhydrous Na₂SO₄ (s), filtered and then concentrated in vacuo. The crude mixture was purified using the ISCO flash chromatography system using a 0-100% EtOAc gradient/100-0% Hexane gradient mixture. Following concentration of the appropriate fractions the crude solid collected was further purified by recrystallization using an Et₂O/Hexane solvent mixture to give the title compound as an off white solid (13 mg, 37%). ¹H NMR (DMSO) δ: 7.92 (s, 1H), 7.45-7.52 (m, 2H), 7.61 (d, J=6.7 Hz, 1H), 7.24-7.31 (m, 2H), 6.28 (s, 2H), 6.37 (d, J=7.0 Hz, 1H), 3.96 (br. S, H), 3.72 (s, 3H), 3.29 (s, 2H), 2.66(t, j=5.3 Hz, 2H), 2.18 (s, 3H).

Example 6

3-(2-amino-7,8-dihydropyrido[4,3-d]pyrimidin-6 (5H)-yl)-1-[4-(2-methoxyethyl)phenyl]-4-methylpyridin-2(1H)-one

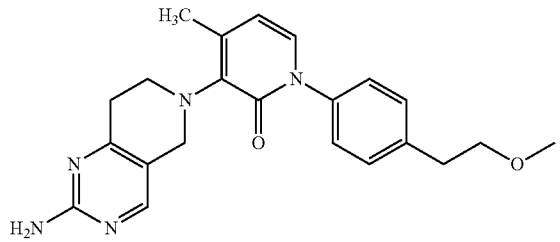 [SMILES: COCCc1ccc(-n2ccc(C)c(N3CCc4nc(N)ncc4C3)c2=O)cc1]

A degassed solution of 3-(2-amino-7,8-dihydropyrido[4, 3-d]pyrimidin-6(5H)-yl)-4-methylpyridin-2(1H)-one (26 mg, 0.099 mmol), N1,N2-dimethylethane-1,2-diamine (6 mg, 0.051 mmol), copper iodide (4 mg, 0.020 mmol), and potassium phosphate (41 mg, 0.194 mmol) in 2 mL of N-methylpyrrolidone was heated to 70° C. After allowing the reaction to stir overnight (12 h) at 70° C., the reaction was cooled to room temperature and was extracted with EtOAc (3×5 mL) and with NaHCO₃ (2×10 mL). The crude organic layers were combined, dried over anhydrous Na₂SO₄ (s), filtered and then concentrated in vacuo. The crude mixture was then purified using the ISCO flash chromatography system using a 0-100% EtOAc gradient/100-0% Hexane gradient mixture. The appropriate fractions were concentrated and then the crude product was further purified by recrystallization using an Et₂O/Hexane solvent mixture, to give the title compound as an off white solid (12 mg, 32%). ¹H NMR (DMSO) δ 7.92 (s, 1H), 7.54-7.65 (m, 2H), 7.51 (d, J=6.7 Hz, 1H), 7.26-7.35 (m, 2H), 6.29 (s, 2H), 6.27 (d, J=7.0 Hz, 1H), 4.02 (br. S, H), 3.81 (m, 5H), 3.30 (s, 2H), 2.55 (t, J=5.3 Hz, 2H), 2.09 (t, J=3.4 Hz, 2H).

Example 7

3-(2-amino-7,8-dihydropyrido[4,3-d]pyrimidin-6 (5H)-yl)-4-methyl-1-(3-thienyl)pyridin-2(1H)-one

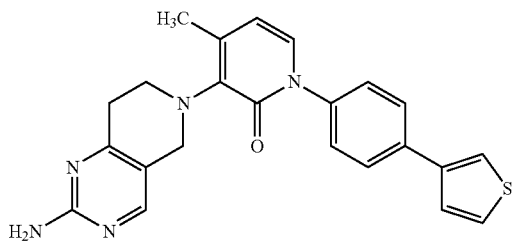 [SMILES: Cc1ccn(-c2ccc(-c3ccsc3)cc2)c(=O)c1N1CCc2nc(N)ncc2C1]

A degassed solution of 3-(2-amino-7,8-dihydropyrido[4, 3-d]pyrimidin-6(5H)-yl)-4-methylpyridin-2(1H)-one (26 mg, 0.097 mmol), 3-iodothiophene (23 mg, 0.102 mmol), N1,N2-dimethylethane-1,2-diamine (5 mg, 0.049 mmol), copper iodide (4 mg, 0.020 mmol), and potassium phosphate (41 mg, 0.194 mmol) in 2 mL of N-methylpyrrolidone was heated to 70° C. After allowing the reaction to stir overnight (16 h) at 70° C., the reaction was complete and therefore allowed to cool to room temperature. The reaction was extracted with with EtOAc (3×5 mL) and with NaHCO₃ (2×10 mL). The crude organic layers were combined, dried over anhydrous Na₂SO₄ (s), filtered and then concentrated in vacuo. The crude mixture was then purified over silica using a 0-100% EtOAc gradient/100-0% Hexane gradient mixture after which, the appropriate fractions were concentrated to afford a solid. This solid was further purified by recrystallization using an Et₂O/Hexane solvent mixture to give the title compound (11 mg, 35%). ¹H NMR (DMSO) δ: 7.98 (s, 1H), 7.92 (s, 1H), 7.84 (d, J=6.2, 1H), 7.22 (d, J=6.2, 1H), 6.28 (m, 1H), 6.17 (d, J=7.0 Hz, 2H), 3.98 (br. S, 2H), 3.33 (s, 2H), 2.56(t, j=5.3 Hz, 2H), 2.17 (s, 3H)

Example 8

3-(2-amino-7,8-dihydropyrido[4,3-d]pyrimidin-6 (5H)-yl)-4-methyl-1-(1-methyl-1H-pyrazol-3-yl)-1, 6-dihydropyridin-2(3H)-one

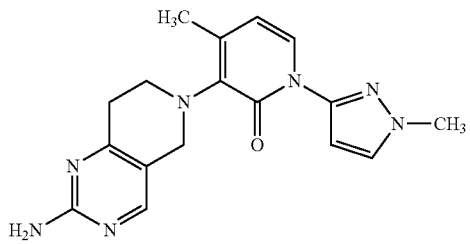 [SMILES: Cc1ccn(-c2ccn(C)n2)c(=O)c1N1CCc2nc(N)ncc2C1]

A degassed solution of 3-(2-amino-7,8-dihydropyrido[4, 3-d]pyrimidin-6(5H)-yl)-4-methylpyridin-2(1H)-one (27 mg, 0.100 mmol), 3-iodo-1-methyl-1H-pyrazole (20 mg, 0.097 mmol), N1,N2-dimethylethane-1,2-diamine (5 mg, 0.049 mmol), copper iodide (4 mg, 0.020 mmol), and potassium phosphate (43 mg, 0.197 mmol) 2 mL of N-methylpyrrolidone was heated to 70° C. After allowing the reaction to stir overnight (17 h) at 70° C., the reaction was complete and allowed to cool to room temperature. The reaction was extracted 3×'s with EtOAc (3×5 mL) and 2×'s with NaHCO$_3$ (3×10 mL). The crude organic layers were combined, dried over anhydrous Na$_2$SO$_4$ (s), filtered and then concentrated in vacuo. The crude mixture was then purified using the ISCO flash chromatography system using a 0-100% EtOAc/100-0% Hexane gradient mixture. A second column was done on the impure product using a gradient of MeOH/CHCl$_3$ after which, the appropriate fractions were concentrated, to afford a yellow solid (17 mg, 52%). $^1$H NMR (DMSO) δ: 8.01 (s, 1H), 7.79 (d, J=6.0, 1H), 6.34 (d, J=6.0, 1H), 6.24 (m, 1H), 6.15 (d, J=7.0 Hz, 2H), 4.00 (br. S, 2H), 3.22 (s, 2H), 2.64(t, j=5.3 Hz, 2H), 2.20 (s, 3H)

Example 9

3-(2-amino-7,8-dihydropyrido[4,3-d]pyrimidin-6 (5H)-yl)-4-methyl-1-(m-tolyl)-1,6-dihydropyridin-2 (3H)-one

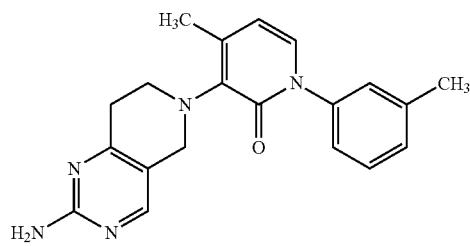 [SMILES: Cc1cccc(-n2ccc(C)c(N3CCc4nc(N)ncc4C3)c2=O)c1]

A degassed solution of 3-(2-amino-7,8-dihydropyrido[4, 3-d]pyrimidin-6(5H)-yl)-4-methylpyridin-2(1H)-one (24 mg, 0.096 mmol), 1-iodo-3-methylbenzene (20 mg, 0.097 mmol), N1,N2-dimethylethane-1,2-diamine (5 mg, 0.049 mmol), copper iodide (5 mg, 0.022 mmol), and potassium phosphate (44 mg, 0.199 mmol) in 2 mL of N-methylpyrrolidone was heated to 70° C. After allowing the reaction to stir overnight (17 h) at 70° C., the reaction was complete and allowed to cool to room temperature. The reaction was extracted with EtOAc (3×5 mL) and with NaHCO$_3$ (2×10 mL). The crude organic layers were combined, dried over anhydrous Na$_2$SO$_4$ (s), filtered and then concentrated in vacuo. The crude mixture was then purified using the ISCO flash chromatography system using a CHCl$_3$/EtOAc gradient. Upon reaching a 1:1 mixture of EtOAc and CHCl$_3$, 3% MeOH was added and increased to 6% MeOH which, after concentrating the appropriate fractions, afforded the title compound as a pale yellow solid (16 mg, 47%). $^1$H NMR (DMSO) δ: 7.99 (s, 1H), 7.80 (d, J=6.0, 1H), 6.56 (d, J=6.0, 1H), 6.28 (m, 1H), 6.20 (d, J=7.0 Hz, 2H), 3.99 (br. S, 2H), 3.31 (s, 2H), 2.66(t, j=5.3 Hz, 2H), 2.15 (s, 3H).

Example 10

3-(2-amino-7,8-dihydropyrido[4,3-d]pyrimidin-6 (5H)-yl)-4-methyl-1-(4-methylphenyl)pyridin-2 (1H)-one

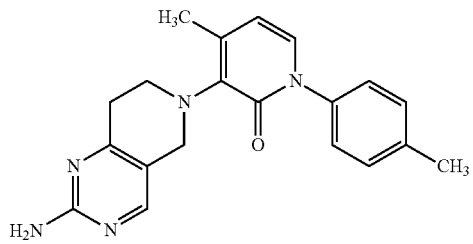 [SMILES: Cc1ccc(-n2ccc(C)c(N3CCc4nc(N)ncc4C3)c2=O)cc1]

A degassed solution of 3-(2-amino-7,8-dihydropyrido[4, 3-d]pyrimidin-6(5H)-yl)-4-methylpyridin-2(1H)-one (25 mg, 0.097 mmol), 1-iodo-4-methylbenzene (20 mg, 0.097 mmol), N1,N2-dimethylethane-1,2-diamine (5 mg, 0.049 mmol), Copper Iodide (5 mg, 0.024 mmol), and Potassium Phosphate (41 mg, 0.194 mmol) 2 mL of N-methylpyrrolidone was heated to 70° C. After allowing the reaction to stir overnight (17 h) at 70° C., the reaction was complete and allowed to cool to room temperature. The reaction was extracted with EtOAc (3×5 mL) and with NaHCO$_3$ (2×10 mL). The crude organic layers were combined, dried over anhydrous Na$_2$SO$_4$ (s), filtered and then concentrated in vacuo. The crude mixture was then purified using the ISCO flash chromatography system using a CHCl$_3$/EtOAc gradient. Upon reaching a 1:1 mixture of EtOAc and CHCl$_3$, 3% MeOH was added and increased to 6% MeOH which, after concentrating the appropriate fractions afforded the title compound as a tan solid (13 mg, 38%). $^1$H NMR (DMSO) δ: 7.90 (s, 1H), 7.50-7.59 (m, 2H), 7.44 (d, J=6.7 Hz, 1H), 7.25-7.32 (m, 2H), 6.19 (s, 2H), 6.08 (d, J=7.0 Hz, 1H), 3.89 (br. S, H), 3.29 (s, 2H), 2.64(t, j=5.3 Hz, 2H), 2.13 (s, 3H), 1.99 (s, 3H).

Example 11

3-(2-amino-7,8-dihydropyrido[4,3-d]pyrimidin-6 (5H)-yl)-4-methyl-1-(2-methylphenyl)pyridin-2 (1H)-one

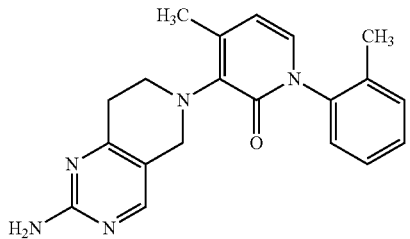 [SMILES: Cc1ccccc1-n1ccc(C)c(N2CCc3nc(N)ncc3C2)c1=O]

A degassed solution of 3-(2-amino-7,8-dihydropyrido[4, 3-d]pyrimidin-6(5H)-yl)-4-methylpyridin-2(1H)-one (0.025 g, 0.097 mmol), 1-iodo-2-methylbenzene (20 mg, 0.097 mmol), N1,N2-dimethylethane-1,2-diamine (6 mg, 0.049 mmol), copper iodide (5 mg, 0.020 mmol), and potassium phosphate (41 mg, 0.194 mmol) in 0.5 mL of N-methylpyrrolidone was heated to 70° C. After allowing the reaction to stir overnight (17 h) at 70° C., the reaction was complete and allowed to cool to room temperature. The reaction was extracted with EtOAc (3×5 mL) and with NaHCO$_3$ (2×10 mL). The crude organic layers were combined, dried over anhydrous Na$_2$SO$_4$ (s), filtered and the concentrated in vacuo. The crude mixture was then purified using the ISCO flash chromatography system using a CHCl$_3$/EtOAc gradient. Upon reaching a 1:1 mixture of EtOAc and CHCl$_3$, 3% MeOH was added and increased up to 6% MeOH. After concentrating the appropriate fractions, a white solid was collected as the pure product (8 mg, 24%). $^1$H NMR (DMSO) δ: 7.92 (s, 1H), 7.45-7.52 (m, 2H), 7.46 (m, 1H), 7.28-7.35 (m, 2H), 6.28 (s, 2H), 6.17 (m, 1H), 3.96 (br. S, H), 3.29 (s, 2H), 2.66(t, j=5.3 Hz, 2H), 2.21 (s, 3H), 2.07 (s, 3H).

Example 12

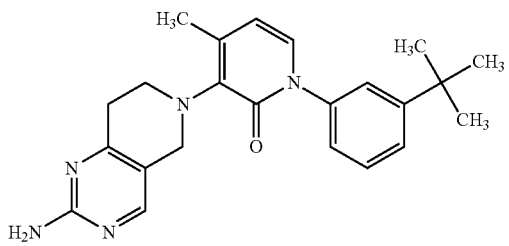 [SMILES: Cc1ccn(-c2cccc(C(C)(C)C)c2)c(=O)c1N1CCc2nc(N)ncc2C1]

3-(2-amino-7,8-dihydropyrido[4,3-d]pyrimidin-6 (5H)-yl)-1-(3-tert-butylphenyl)-4-methylpyridin-2 (1H)-one A degassed solution of 3-(2-amino-7,8-dihydropyrido[4, 3-d]pyrimidin-6(5H)-yl)-4-methylpyridin-2(1H)-one (0.025 g, 0.097 mmol), 1-iodo-3-tertbutyl benzene (0.20 g, 0.097 mmol), N1,N2-dimethylethane-1,2-diamine (0.005 g, 0.049 mmol), Copper Iodide (0.004 g, 0.020 mmol), and Potassium Phosphate (0.041 g, 0.194 mmol) in 0.5 mL of N-methylpyrrolidone was heated to 70° C. After allowing the reaction to stir overnight (17 h) at 70° C., the reaction was complete and allowed to cool to room temperature. The reaction was extracted with 3×'s with EtOAc (~5 mL) and 2×'s with NaHCO$_3$ (~10 mL). The crude organic layers were combined, dried over anhydrous Na$_2$SO$_4$ (s), filtered and the concentrated in vacuo. The crude mixture was then purified using the ISCO flash chromatography system using an 0-100% EtOAc gradient/100-0% Hexane gradient mixture. After concentrating the appropriate fractions, the pure product was collected as an off white solid (5 mg, 19%). $^1$H NMR (DMSO) δ: 7.94 (s, 1H), 7.46-7.55 (m, 2H), 7.47 (m, 1H), 7.28-7.36 (m, 2H), 6.32 (s, 2H), 6.21 (m, 1H), 3.96 (br. S, H), 3.29 (s, 2H), 2.66(t, j=5.3 Hz, 2H), 2.25 (s, 3H), 2.09 (s, 9H).

Example 13

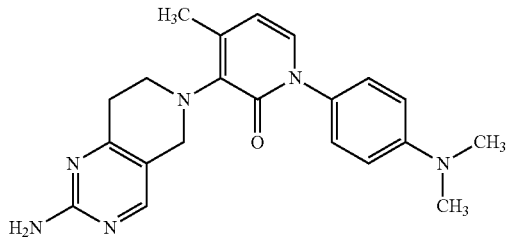 [SMILES: Cc1ccn(-c2ccc(N(C)C)cc2)c(=O)c1N1CCc2nc(N)ncc2C1]

3-(2-amino-7,8-dihydropyrido[4,3-d]pyrimidin-6 (5H)-yl)-1-[4-(dimethylamino)phenyl]-4-methylpyridin-2(1H)-one A degassed solution of 3-(2-amino-7,8-dihydropyrido[4, 3-d]pyrimidin-6(5H)-yl)-4-methylpyridin-2(1H)-one (25 mg, 0.097 mmol), 4-iodo-N,N-dimethylaniline (20 mg, 0.097 mmol), N1,N2-dimethylethane-1,2-diamine (5 mg, 0.049 mmol), copper iodide (5 mg, 0.020 mmol), and potassium phosphate (40 mg, 0.191 mmol) in 0.5 mL of N-methylpyrrolidone was heated to 70° C. After allowing the reaction to stir overnight (15 h) at 70° C., the reaction was complete and allowed to cool to room temperature. The reaction was extracted with EtOAc (3×5 mL) and with NaHCO$_3$ (2×10 mL). The crude organic layers were combined, dried over anhydrous Na$_2$SO$_4$ (s), filtered and the concentrated in vacuo. The crude mixture was then purified using the ISCO flash chromatography system using an 0-100% gradient EtOAc/ 100-0% gradient Hexane. Following concentration of the appropriate fractions in vacuo the product was further purified by recrystallization using a Et$_2$O/Hexane solvent mixture to give the title compound as a light grey solid (15 mg, 39%). $^1$H NMR (DMSO) δ: 7.90 (s, 1H), 7.46-7.53 (m, 2H), 7.43 (d, J=6.7 Hz, 1H), 7.22-7.30 (m, 2H), 6.28 (s, 2H), 6.17 (d, J=7.0 Hz, 1H), 3.96 (br. S, H), 3.29 (s, 2H), 3.02 (s, 6H) 2.65(t, j=5.3 Hz, 2H), 2.17 (s, 3H).

Example 14

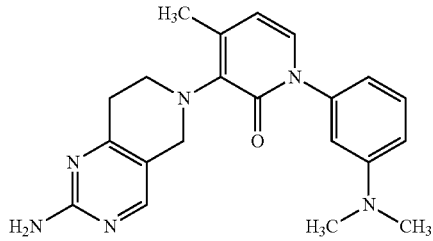 [SMILES: Cc1ccn(-c2cccc(N(C)C)c2)c(=O)c1N1CCc2nc(N)ncc2C1]

3-(2-amino-7,8-dihydropyrido[4,3-d]pyrimidin-6 (5H)-yl)-1-[3-(dimethylamino)phenyl]-4-methylpyridin-2(1H)-one A degassed solution of 3-(2-amino-7,8-dihydropyrido[4, 3-d]pyrimidin-6(5H)-yl)-4-methylpyridin-2(1H)-one (25 mg, 0.097 mmol), 3-iodo-N,N-dimethylaniline (20 mg, 0.097 mmol), N1,N2-dimethylethane-1,2-diamine (5 mg, 0.049 mmol), copper iodide (5 mg, 0.020 mmol), and potassium phosphate (44 mg, 0.206 mmol) in 0.5 mL of N-methylpyrrolidone was heated to 70° C. After allowing the reaction to stir overnight (13 h) at 70° C., the reaction was complete and allowed to cool to room temperature. The reaction was extracted with EtOAc (3×5 mL) and with NaHCO₃ (2×10 mL). The crude organic layers were combined, dried over anhydrous Na₂SO₄ (s), filtered and the concentrated in vacuo. The crude mixture was then purified using the ISCO flash chromatography system using a 0-100% EtOAc gradient/ 100-0% Hexane gradient. The fractions containing the product were concentrated in vacuo and then further purified by recrystallization using an Et₂O/Hexane solvent mixture to give the title compound (13 mg, 37%). ¹H NMR (DMSO) δ: 7.92 (s, 1H), 7.45-7.52 (m, 2H), 7.46 (m, 1H), 7.28-7.35 (m, 2H), 6.28 (s, 2H), 6.17 (m, 1H), 3.96 (br. S, H), 3.29 (s, 2H), 3.00 (s, 6H), 2.66 (t, j=5.3 Hz, 2H), 2.18 (s, 3H).

Example 15

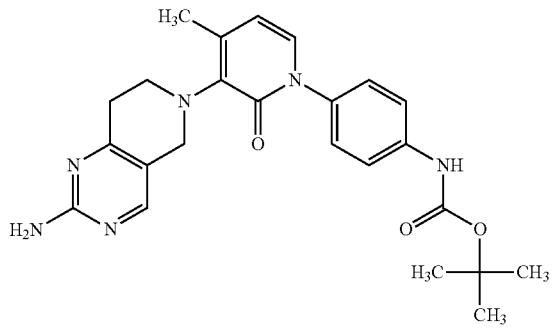 [SMILES: Cc1ccn(-c2ccc(NC(=O)OC(C)(C)C)cc2)c(=O)c1N1CCc2nc(N)ncc2C1]

tert-butyl {4-[3-(2-amino-7,8-dihydropyrido[4,3-d]pyrimidin-6(5H)-yl)-4-methyl-2-oxopyridin-1(2H)-yl]phenyl}carbamate A degassed solution of 3-(2-amino-7,8-dihydropyrido[4,3-d]pyrimidin-6(5H)-yl)-4-methylpyridin-2(1H)-one (250 mg, 0.97 mmol), tert-butyl(4-iodophenyl)carbamate (200 mg, 0.97 mmol), N1,N2-dimethylethane-1,2-diamine (50 mg, 0.49 mmol), copper iodide (40 mg, 0.20 mmol), and potassium phosphate (410 mg, 1.94 mmol) in 2.0 mL of N-methylpyrrolidone was heated to 70° C. After allowing the reaction to stir overnight (17 h) at 70° C., the reaction was complete and allowed to cool to room temperature. The reaction was extracted with EtOAc (3×5 mL) and 2×'s with NaHCO₃ (2×10 mL). The crude organic layers were combined, dried over anhydrous Na₂SO₄, filtered and the concentrated in vacuo. The crude mixture was then purified using the ISCO flash chromatography system using an 0-100% EtOAc/ 100-0% Hexane gradient mixture. Following concentration of the appropriate fractions the title compound was collected as an off white solid (150 mg, 33%). ¹H NMR (DMSO) δ: 9.52 (s, 1H), 7.92 (s, 1H), 7.45-7.52 (m, 2H), 7.41 (d, J=6.7 Hz, 1H), 7.24-7.31 (m, 2H), 6.28 (s, 2H), 6.17 (d, J=7.0 Hz, 1H), 3.96 (br. S, H), 3.29 (s, 2H), 2.66(t, j=5.3 Hz, 2H), 2.18 (s, 3H), 1.39 (s, 9H).

Example 16

3-(2-amino-7,8-dihydropyrido[4,3-d]pyrimidin-6 (5H)-yl)-1-(4-aminophenyl)-4-methylpyridin-2(1H)-one

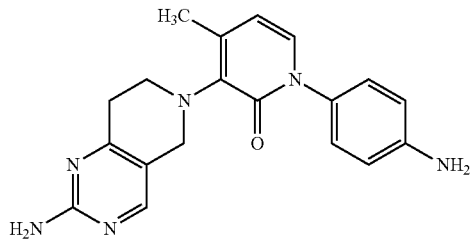 [SMILES: Cc1ccn(-c2ccc(N)cc2)c(=O)c1N1CCc2nc(N)ncc2C1]

Tert-butyl (4-(5-(2-amino-7,8-dihydropyrido[4,3-d]pyrimidin-6(5H)-yl)-4-methyl-6-oxo-5,6-dihydropyridin-1 (2H)-yl)phenyl)carbamate (150 mg, 0.334 mmol) was dissolved into a 1:1 mixture of MeOH/THF (~10 mL) and treated with CF₃COOH drop wise and the reaction was allowed to stir for 4 h. One the reaction was completed, the residual CF₃COOH was neutralized with NaHCO₃ (aq). The reaction was then extracted with EtOAc (3×10 mL) and brine (~10 mL). The combined organic layers were dried over anhydrous Na₂SO₄, filtered and then concentrated in vacuo. The crude organic oil was then purified via column chromatography (MeOH/CHCl₃ gradient). Concentration of the appropriate fractions provided the title compound (102 mg, 88%). ¹H NMR (DMSO) δ: 7.92 (s, 1H), 7.45-7.52 (m, 2H), 7.41 (d, J=6.7 Hz, 1H), 7.24-7.31 (m, 2H), 6.28 (s, 2H), 6.17 (d, J=7.0 Hz, 1H), 3.96 (br. S, H), 3.29 (s, 2H), 2.66 (t, j=5.3 Hz, 2H), 2.18 (s, 3H).

Example 17

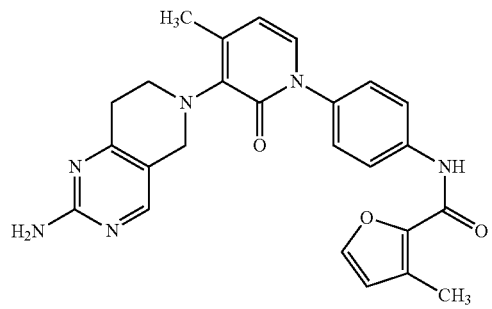 [SMILES: Cc1ccoc1C(=O)Nc1ccc(-n2ccc(C)c(N3CCc4nc(N)ncc4C3)c2=O)cc1]

N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide A solution of 3-(2-amino-7,8-dihydropyrido[4,3-d]pyrimidin-6(5H)-yl)-1-(4-aminophenyl)-4-methylpyridin-2 (1H)-one (25 mg, 0.075 mmol) in2 mL of THF under N₂(g)

containing 3 mL of NEt₃ was treated with 3-methylfuran-2-carbonyl chloride (13 mg, 0.090 mmol). The reaction mixture was heated to 40° C. and allowed to stir for 3 h. The reaction was cooled and then extracted with EtOAc (3×~10 mL) and water (~10 mL). The combined organic layers were then washed with ~20 mL of NaHCO₃ (aq). The organic layers were then dried over anhydrous Na₂SO₄, filtered and then concentrated in vacuo. The crude mixture was purified over silica (EtOAc/Hexanes gradient). Following concentration of the appropriate fractions the title compound was collected as a grey solid (25 mg, 76%). ¹H NMR (DMSO) δ: 9.52 (s, 1H), 7.92 (s, 1H), 7.81 (d, J=5.6 Hz, 1H), 7.45-7.52 (m, 2H), 7.41 (d, J=6.7 Hz, 1H), 7.24-7.31 (m, 2H), 6.65 (d, J=5.6 Hz, 1H), 6.28 (s, 2H), 6.17 (d, J=7.0 Hz, 1H), 3.96 (br. S, H), 3.29 (s, 2H), 2.66(t, j=5.3 Hz, 2H), 2.35 (s, 3H), 2.18 (s, 3H).

Example 18

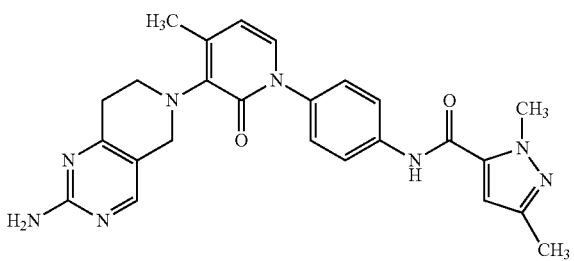 [SMILES: Cc1cc(C(=O)Nc2ccc(-n3ccc(C)c(N4CCc5nc(N)ncc5C4)c3=O)cc2)n(C)n1]

N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide A solution of 3-(2-amino-7,8-dihydropyrido[4,3-d]pyrimidin-6(5H)-yl)-1-(4-aminophenyl)-4-methylpyridin-2(1H)-one (26 mg, 0.078 mmol) in THF (3 mL) and NEt₃ (3 mL) was treated with 1,3-dimethyl-1H-pyrazole-5-carbonyl chloride (16 mg, 0.105 mmol). The reaction was heated to 40° C. and allowed to stir for 5 h. The reaction was cooled and then extracted with EtOAc (3×~10 mL) and water (~10 mL). The combined organic layers were then washed with ~20 mL of NaHCO₃(aq). The organic layers were then dried over anhydrous Na₂SO₄, filtered and then concentrated in vacuo. The crude mixture was purified over silica (EtOAc/Hexanes gradient). Following concentration of the appropriate fractions the title compound was collected as a grey solid (25 mg, 76%). ¹H NMR (DMSO) δ: 9.52 (s, 1H), 7.92 (s, 1H), 7.81 (d, J=5.6 Hz, 1H), 7.45-7.52 (m, 2H), 7.41 (d, J=6.7 Hz, 1H), 7.24-7.31 (m, 2H), 6.65 (d, J=5.6 Hz, 1H), 6.28 (s, 2H), 6.17 (d, J=7.0 Hz, 1H), 3.96 (br. S, H), 3.29 (s, 2H), 2.66(t, j=5.3 Hz, 2H), 2.35 (s, 3H), 2.18 (s, 3H).

Example 19

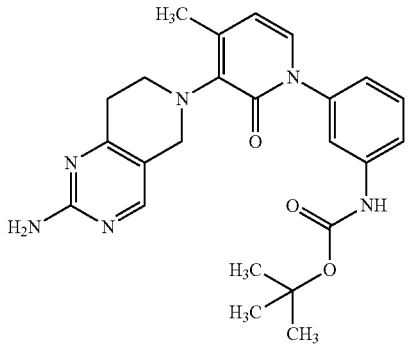 [SMILES: Cc1ccn(-c2cccc(NC(=O)OC(C)(C)C)c2)c(=O)c1N1CCc2nc(N)ncc2C1]

tert-butyl {4-[3-(2-amino-7,8-dihydropyrido[4,3-d]pyrimidin-6(5H)-yl)-4-methyl-2-oxopyridin-1(2H)-yl]phenyl}carbamate A degassed solution of 3-(2-amino-7,8-dihydropyrido[4,3-d]pyrimidin-6(5H)-yl)-4-methylpyridin-2(1H)-one (250 mg, 0.97 mmol), tert-butyl(4-iodophenyl)carbamate (200 mg, 0.97 mmol), N1,N2-dimethylethane-1,2-diamine (50 mg, 0.49 mmol), copper iodide (40 mg, 0.20 mmol), and potassium phosphate (410 mg, 1.94 mmol) in 2 mL of N-methylpyrrolidone was heated to 70° C. and stirred overnight (17 h). The reaction was complete and allowed to cool to room temperature. The reaction was extracted with EtOAc (3×~5 mL) and with NaHCO3 (2×~10 mL). The crude organic layers were combined, dried over anhydrous Na₂SO₄ (s), filtered and the concentrated in vacuo. The crude mixture was then purified using the ISCO flash chromatography system using an 0-100% EtOAc/100-0% Hexane gradient mixture. Following concentration of the appropriate fractions the desired product was collected as an off white solid (115 mg, 27%). ¹H NMR (DMSO) δ: 9.52 (s, 1H), 7.92 (s, 1H), 7.45-7.52 (m, 2H), 7.41 (d, J=6.7 Hz, 1H), 7.24-7.31 (m, 2H), 6.28 (s, 2H), 6.17 (d, J=7.0 Hz, 1H), 3.96 (br. S, H), 3.29 (s, 2H), 2.66(t, j=5.3 Hz, 2H), 2.18 (s, 3H), 1.39 (s, 9H)

Example 20

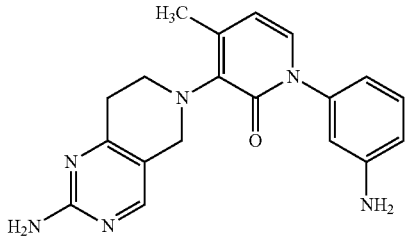 [SMILES: Cc1ccn(-c2cccc(N)c2)c(=O)c1N1CCc2nc(N)ncc2C1]

3-(2-amino-7,8-dihydropyrido[4,3-d]pyrimidin-6(5H)-yl)-1-(4-aminophenyl)-4-methylpyridin-2(1H)-one A solution of tert-butyl (4-(5-(2-amino-7,8-dihydropyrido[4,3-d]pyrimidin-6(5H)-yl)-4-methyl-6-oxo-5,6-dihydropyridin-1(2H)-yl)phenyl)carbamate (112 mg, 0.334 mmol) in a 1:1 mixture of MeOH/THF (~10 mL) was treated dropwise with CF3COOH and the reaction was allowed to stir for 4 h. One the reaction was completed, the residual CF$_3$COOH was neutralized with NaHCO3 (aq). The reaction was then extracted with EtOAc (3×~10 mL) and brine (~10 mL). The combined organic layers were dried over anhydrous Na$_2$SO$_4$ (s), filtered and the concentrated in vacuo. The crude organic oil was then purified via column chromatography (MeOH/CHCl3 gradient). Following concentration of the appropriate fractions the title compound was isolated (112 mg, 88%). $^1$H NMR (DMSO) δ: 7.91 (s, 1H), 7.80(m, 1H), 7.41-7.52 (m, 2H), 7.41 (m, 1H), 7.26-7.32 (m, 2H), 6.65(m, 1H), 6.23 (s, 2H), 6.14 (m, 1H), 4.00 (br. s, H), 3.24 (s, 2H), 2.67 (t, J=5.3 Hz, 2H), 2.34 (s, 3H), 2.22 (s, 3H).

Example 21

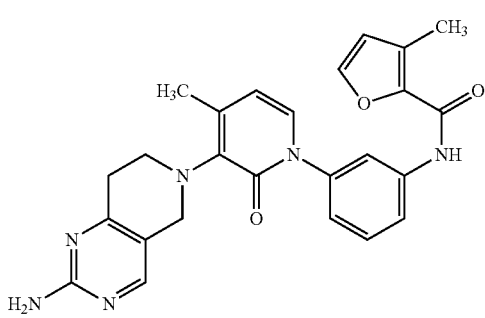 [SMILES: Cc1ccoc1C(=O)Nc1cccc(-n2ccc(C)c(N3CCc4nc(N)ncc4C3)c2=O)c1]

N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide A solution of 3-(2-amino-7,8-dihydropyrido[4,3-d]pyrimidin-6(5H)-yl)-1-(4-aminophenyl)-4-methylpyridin-2(1H)-one (25 mg, 0.075 mmol) was dissolved in THF (2 mL) and NEt$_3$ (3 mL) and then treated with 3-methylfuran-2-carbonyl chloride (13 mg, 0.090 mmol). The reaction was heated to 40° C. and allowed to stir for 3 h. The reaction was cooled and then extracted with EtOAc (3×~10 mL) and water (~10 mL). The combined organic layers were then washed with ~20 mL of NaHCO$_3$(aq). The organic layers were then dried over anhydrous Na$_2$SO$_4$ (s), filtered and the concentrated in vacuo. The crude mixture was purified over silica (EtOAc/Hexanes gradient). Following concentration of the appropriate fractions the title compound was isolated as a grey solid (25 mg, 76%). $^1$H NMR (DMSO) δ: 9.52 (s, 1H), 7.92 (s, 1H), 7.80(m, 1H), 7.42-7.52 (m, 2H), 7.41 (m, 1H), 7.24-7.32 (m, 2H), 6.66 (m, 1H), 6.28 (s, 2H), 6.14 (m, 1H), 4.01 (br. s, H), 3.24 (s, 2H), 2.67 (t, J=5.3 Hz, 2H), 2.35 (s, 3H), 2.20 (s, 3H).

Example 22

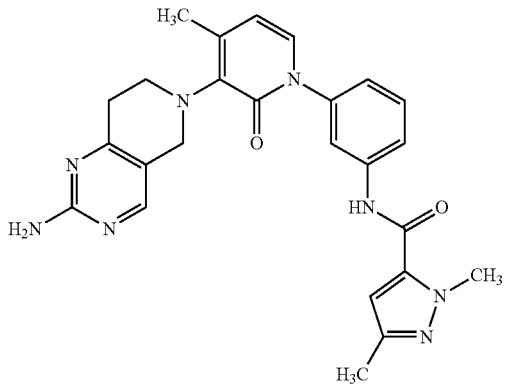 [SMILES: Cc1cc(C(=O)Nc2cccc(-n3ccc(C)c(N4CCc5nc(N)ncc5C4)c3=O)c2)n(C)n1]

N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide A solution of 3-(2-amino-7,8-dihydropyrido[4,3-d]pyrimidin-6(5H)-yl)-1-(4-aminophenyl)-4-methylpyridin-2(1H)-one (26 mg, 0.078 mmol) in 3 mL of THF (3 mL) and NEt$_3$ (3 mL) was treated with 1,3-dimethyl-1H-pyrazole-5-carbonyl chloride (16 mg, 0.105 mmol). The reaction was heated to 40° C. and allowed to stir for 5 h. The reaction was cooled and then extracted with EtOAc (3×~10 mL) and water (~10 mL). The combined organic layers were then washed with ~20 mL of NaHCO$_3$(aq). The organic layers were then dried over anhydrous Na$_2$SO$_4$ (s), filtered and the concentrated in vacuo. The crude mixture was purified over silica (EtOAc/Hexanes gradient). Following concentration of the appropriate fractions the title compound was isolated as a grey solid (25 mg, 76%). $^1$H NMR (DMSO) δ: 9.52 (s, 1H), 7.92 (s, 1H), 7.78(m, 1H), 7.45-7.52 (m, 2H), 7.44 (m, 1H), 7.24-7.32 (m, 2H), 6.65 (m, 1H), 6.28 (s, 2H), 6.17 (m, 1H), 3.96 (br. s, H), 3.29 (s, 2H), 2.66 (t, J=5.3 Hz, 2H), 2.35 (s, 3H), 2.18 (s, 3H).

VEGFR2 kinase potency of select analogs was determined by the following assay:

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM MgCl$_2$, 0.1 mM MnCl$_2$ and 0.2 mM Na$_3$VO$_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

PDGFRβ Kinase Assay

Biochemical PDGFR3 kinase assays were performed in 96 well microtiter plates that were coated overnight with 75 µg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 µL reaction volumes containing 36 µM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 100 µl of a monoclonal anti-phosphotyrosine antibody-peroxidase conjugate diluted 1:10,000 in PBS-T was added to the wells for 30 minutes. Following a 2 mls per well wash with PBS-Tween-20, 100 µl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

TABLE 2

In vitro VEGFR2 and PDGFR data

| Example Number | Structure | VEGFR2 Kinase $IC_{50}$ nM | PDGFR Kinase $IC_{50}$ nM |
|---|---|---|---|
| 2 | 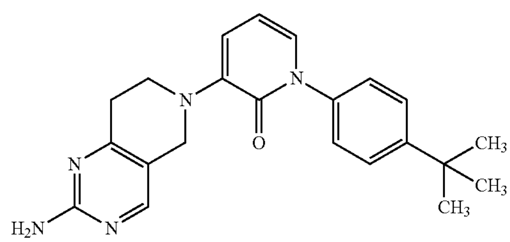 [SMILES: CC(C)(C)c1ccc(-n2cccc(N3CCc4nc(N)ncc4C3)c2=O)cc1] | 286 | 655 |
| 3 | 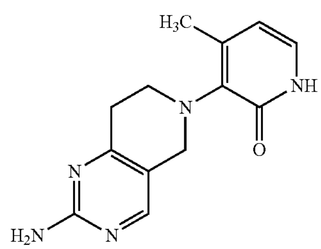 | >10000 | 3887 |
| 4 | 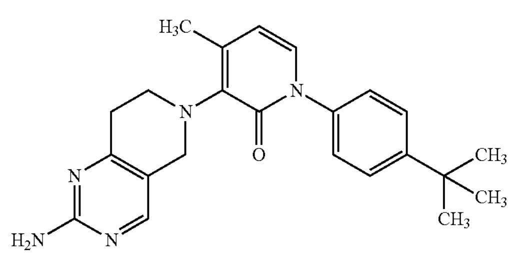 [SMILES: Cc1ccn(-c2ccc(C(C)(C)C)cc2)c(=O)c1N1CCc2nc(N)ncc2C1] | 86 | 381 |
| 14 | 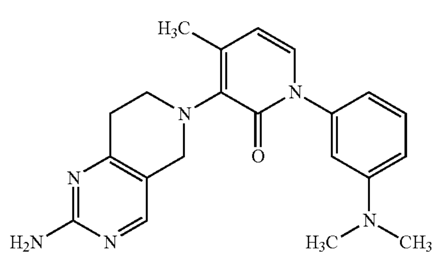 [SMILES: Cc1ccn(-c2cccc(N(C)C)c2)c(=O)c1N1CCc2nc(N)ncc2C1] | 327 | >1000 |

TABLE 2-continued

In vitro VEGFR2 and PDGFR data

| Example Number | Structure | VEGFR2 Kinase IC$_{50}$ nM | PDGFR Kinase IC$_{50}$ nM |
|---|---|---|---|
| 17 | 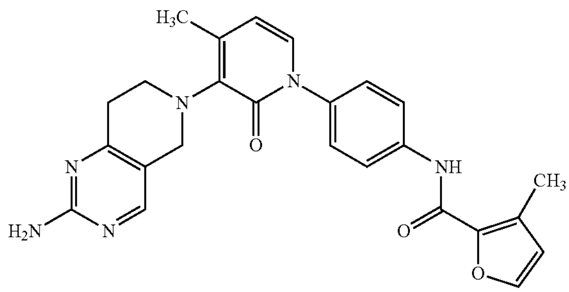 [SMILES: Cc1ccoc1C(=O)Nc1ccc(-n2ccc(C)c(N3CCc4nc(N)ncc4C3)c2=O)cc1] | 29 | 33 |

The fibrotic disorder is selected from the group consisting of hepatic cirrhosis and atherosclerosis.

The mesangial cell proliferative disorder is selected from the group consisting of glomerulonephritis, diabetic nephropathy, malignant nephrosclerosis, thrombotic microangiopathy syndromes, transplant rejection and glomerulopathies.

The metabolic disease is selected from the group consisting of psoriasis, diabetes mellitus, wound healing, inflammation and neurodegenerative diseases.

The blood vessel proliferative disorder is selected from the group consisting of diabetic retinopathy, exudative age-related macular degeneration, retinopathy of prematurity, pterigium, rosacea, arthritis and restenosis.

We claim:

1. A compound represented by Formula I, its enantiomers, diastereoisomers, tautomers, or a pharmaceutically acceptable salt thereof:

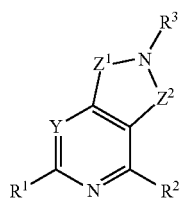

I wherein:
R$^1$ is hydrogen, substituted or unsubstituted C$_{1-12}$ alkyl, halogen, or NR$^9$R$^{10}$;
R$^2$ is hydrogen or NH$_2$;
R$^3$ is represented by one of the formulae below:

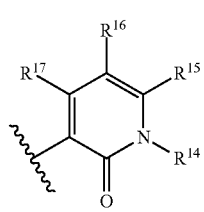

II

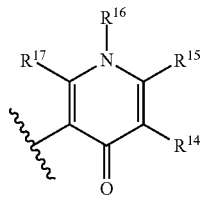

III

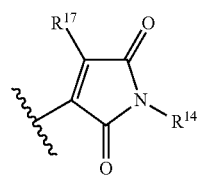

IV

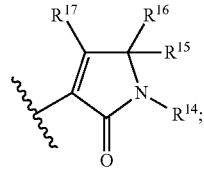

V

Z$^1$ is (CR$^4$R$^5$)$_n$;
Z$^2$ is (CR$^6$R$^7$)$_m$;
Y is N;
n is 2;
m is 1;
R$^4$ is hydrogen or substituted or unsubstituted C$_{1-7}$ alkyl;
R$^5$ is hydrogen or substituted or unsubstituted C$_{1-7}$ alkyl;
R$^6$ is hydrogen or substituted or unsubstituted C$_{1-7}$ alkyl;
R$^7$ is hydrogen or substituted or unsubstituted C$_{1-7}$ alkyl;
R$^9$ is hydrogen, substituted or unsubstituted C$_{1-7}$ alkyl, substituted or unsubstituted aryl, or together with the N and R$^{10}$ can form a substituted or unsubstituted heterocyclic ring;
R$^{10}$ is hydrogen, substituted or unsubstituted C$_{1-7}$ alkyl or together with the N and R$^9$ can form a substituted or unsubstituted heterocyclic ring;
R$^{14}$ is hydrogen, substituted or unsubstituted C$_{1-12}$ alkyl, substituted or unsubstituted heterocycle or substituted or unsubstituted aryl;
R$^{15}$ is hydrogen, substituted or unsubstituted C$_{1-7}$ alkyl, halogen or trifluoromethyl;
R$^{16}$ is hydrogen, substituted or unsubstituted C$_{1-7}$ alkyl, halogen or trifluoromethyl;

$R^{17}$ is hydrogen, substituted or unsubstituted $C_{1-7}$ alkyl, halogen or trifluoromethyl.

2. The compound according to claim 1, wherein:
$R^1$ is $NR^9R^{10}$;
$R^2$ is hydrogen;
$R^3$ is

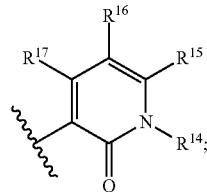

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is hydrogen;
$R^{15}$ is hydrogen;
$R^{16}$ is hydrogen;
$R^{17}$ is hydrogen.

3. The compound according to claim 1, wherein:
$R^1$ is $NR^9R^{10}$;
$R^2$ is hydrogen;
$R^3$ is

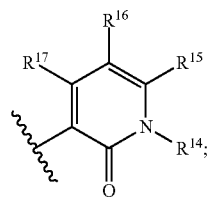

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is substituted or unsubstituted $C_{1-12}$ alkyl;
$R^{15}$ is hydrogen;
$R^{16}$ is hydrogen;
$R^{17}$ is hydrogen.

4. The compound according to claim 1, wherein:
$R^1$ is $NR^9R^{10}$;
$R^2$ is hydrogen;
$R^3$ is

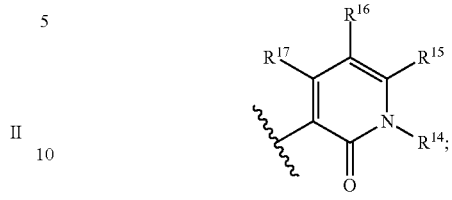

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is hydrogen;
$R^{10}$ is hydrogen;
$R^{14}$ is hydrogen;
$R^{15}$ is hydrogen;
$R^{16}$ is hydrogen;
$R^{17}$ is substituted or unsubstituted $C_{1-7}$ alkyl.

5. The compound according to claim 1, wherein:
$R^1$ is $NR^9R^{10}$;
$R^2$ is hydrogen;
$R^3$ is

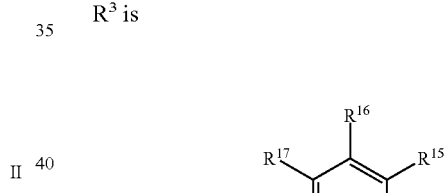

$Z^1$ is $(CR^4R^5)_n$;
$Z^2$ is $(CR^6R^7)_m$;
Y is N;
n is 2;
m is 1;
$R^4$ is hydrogen;
$R^5$ is hydrogen;
$R^6$ is hydrogen;
$R^7$ is hydrogen;
$R^9$ is substituted or unsubstituted $C_{1-7}$ alkyl;
$R^{10}$ is hydrogen;
$R^{14}$ is substituted or unsubstituted $C_{1-12}$ alkyl;
$R^{15}$ is hydrogen;
$R^{16}$ is hydrogen;
$R^{17}$ is substituted or unsubstituted $C_{1-7}$ alkyl.

6. The compound according to claim 1, wherein:
$R^1$ is $NR^9R^{10}$;
$R^2$ is hydrogen;

R³ is

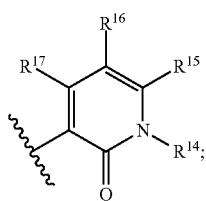

Z¹ is (CR⁴R⁵)$_n$;
Z² is (CR⁶R⁷)$_m$;
Y is N;
n is 2;
m is 1;
R⁴ is hydrogen;
R⁵ is hydrogen;
R⁶ is hydrogen;
R⁷ is hydrogen;
R⁹ is hydrogen;
R¹⁰ is substituted or unsubstituted C$_{1-7}$ alkyl;
R¹⁴ is substituted or unsubstituted heterocycle;
R¹⁵ is hydrogen;
R¹⁶ is hydrogen;
R¹⁷ is substituted or unsubstituted C$_{1-7}$ alkyl.

7. The compound according to claim 1, wherein:
R¹ is NR⁹R¹⁰;
R² is hydrogen;
R³ is

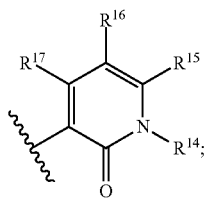

Z¹ is (CR⁴R⁵)$_n$;
Z² is (CR⁶R⁷)$_m$;
Y is N;
n is 2;
m is 1;
R⁴ is hydrogen;
R⁵ is hydrogen;
R⁶ is hydrogen;
R⁷ is hydrogen;
R⁹ is substituted or unsubstituted C$_{1-7}$ alkyl;
R¹⁰ is hydrogen;
R¹⁴ is substituted or unsubstituted aryl;
R¹⁵ is hydrogen;
R¹⁶ is hydrogen;
R¹⁷ is substituted or unsubstituted C$_{1-7}$ alkyl.

8. A compound according to claim 1, selected from:
3-(2-amino-7,8-dihydropyrido[4,3-d]pyrimidin-6(5H)-yl)-1-(4-(tert-butyl)phenyl)pyridin-2(1H)-one;
3-(2-amino-7,8-dihydropyrido[4,3-d]pyrimidin-6(5H)-yl)--(4-tert-butylphenyl)-4-methylpyridin-2(1H)-one;
3-(2-amino-7,8-dihydropyrido[4,3-d]pyrimidin-6(5H)-yl)-1-(4-methoxyphenyl)-4-methylpyridin-2(1H)-one;
3-(2-amino-7,8-dihydropyrido[4,3-d]pyrimidin-6(5H)-yl)-1-[4-(2-methoxyethyl)phenyl]-4-methylpyridin-2(1H)-one;
3-(2-amino-7,8-dihydropyrido[4,3-d]pyrimidin-6(5H)-yl)-4-methyl-1-(3-thienyl)pyridin-2(1H)-one;
3-(2-amino-7,8-dihydropyrido[4,3-d]pyrimidin-6(5H)-yl)-4-methyl-1-(1-methyl-1H-pyrazol-3-yl)-1,6-dihydropyridin-2(3H)-one;
3-(2-amino-7,8-dihydropyrido[4,3-d]pyrimidin-6(5H)-yl)-4-methyl-1-(m-tolyl)-1,6-dihydropyridin-2(3H)-one;
3-(2-amino-7,8-dihydropyrido[4,3-d]pyrimidin-6(5H)-yl)-4-methyl-1-(4-methylphenyl)pyridin-2(1H)-one;
3-(2-amino-7,8-dihydropyrido[4,3-d]pyrimidin-6(5H)-yl)-4-methyl-1-(2-methylphenyl)pyridin-2(1H)-one;
3-(2-amino-7,8-dihydropyrido[4,3-d]pyrimidin-6(5H)-yl)-1-(3-tert-butylphenyl)-4-methylpyridin-2(1H)-one;
3-(2-amino-7,8-dihydropyrido[4,3-d]pyrimidin-6(5H)-yl)-1-[4-(dimethylamino)phenyl]-4-methylpyridin-2(1H)-one;
3-(2-amino-7,8-dihydropyrido[4,3-d]pyrimidin-6(5H)-yl)-1-[3-(dimethylamino)phenyl]-4-methylpyridin-2(1H)-one;
tert-butyl {4-[3-(2-amino-7,8-dihydropyrido[4,3-d]pyrimidin-6(5H)-yl)-4-methyl-2-oxopyridin-1(2H)-yl]phenyl}carbamate;
3-(2-amino-7,8-dihydropyrido[4,3-d]pyrimidin-6(5H)-yl)-1-(4-aminophenyl)-4-methylpyridin-2(1H)-one;
N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide;
N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide;
tert-butyl {4-[3-(2-amino-7,8-dihydropyrido[4,3-d]pyrimidin-6(5H)-yl)-4-methyl-2-oxopyridin-1(2H)-yl]phenyl}carbamate;
3-(2-amino-7,8-dihydropyrido[4,3-d]pyrimidin-6(5H)-yl)-1-(4-aminophenyl)-4-methylpyridin-2(1H)-one;
N-{4-[3-(2-amino-7,8-dihydropyrido[4,3-d]pyrimidin-6(5H)-yl)-4-methyl-2-oxopyridin-1(2H)-yl]phenyl}-3-methyl-2-furamide;
N-{4-[3-(2-amino-7,8-dihydropyrido[4,3-d]pyrimidin-6(5H)-yl)-4-methyl-2-oxopyridin-1(2H)-yl]phenyl}-1,3-dimethyl-1H-pyrazole-5-carboxamide;
N-{4-[3-(2-amino-7,8-dihydropyrido[4,3-d]pyrimidin-6(5H)-yl)-4-methyl-2-oxopyridin-1(2H)-yl]phenyl}-2-methylbenzamide;
N-{4-[3-(2-amino-7,8-dihydropyrido[4,3-d]pyrimidin-6(5H)-yl)-4-methyl-2-oxopyridin-1(2H)-yl]phenyl}-4-chlorobenzamide;
N-{4-[3-(2-amino-7,8-dihydropyrido[4,3-d]pyrimidin-6(5H)-yl)-4-methyl-2-oxopyridin-1(2H)-yl]phenyl}-3-chloro-4-fluorobenzamide;
N-{4-[3-(2-amino-7,8-dihydropyrido[4,3-d]pyrimidin-6(5H)-yl)-4-methyl-2-oxopyridin-1(2H)-yl]phenyl}-3-(methylthio)benzamide;
N-{4-[3-(2-amino-7,8-dihydropyrido[4,3-d]pyrimidin-6(5H)-yl)-4-methyl-2-oxopyridin-1(2H)-yl]phenyl}-4-chloro-3-(trifluoromethyl)benzamide;
N-{4-[3-(2-amino-7,8-dihydropyrido[4,3-d]pyrimidin-6(5H)-yl)-4-methyl-2-oxopyridin-1(2H)-yl]phenyl}-3-(trifluoromethyl)benzamide;
N-{4-[3-(2-amino-7,8-dihydropyrido[4,3-d]pyrimidin-6(5H)-yl)-4-methyl-2-oxopyridin-1(2H)-yl]phenyl}benzamide;

N-{4-[3-(2-amino-7,8-dihydropyrido[4,3-d]pyrimidin-6(5H)-yl)-4-methyl-2-oxopyridin-1(2H)-yl]phenyl}-3-bromobenzamide;

N-{4-[3-(2-amino-7,8-dihydropyrido[4,3-d]pyrimidin-6(5H)-yl)-4-methyl-2-oxopyridin-1(2H)-yl]phenyl}-3-methoxybenzamide;

N-{4-[3-(2-amino-7,8-dihydropyrido[4,3-d]pyrimidin-6(5H)-yl)-4-methyl-2-oxopyridin-1(2H)-yl]phenyl}-3-methylthiophene-2-carboxamide;

N-{4-[3-(2-amino-7,8-dihydropyrido[4,3-d]pyrimidin-6(5H)-yl)-4-methyl-2-oxopyridin-1(2H)-yl]phenyl}-3-methylbenzamide;

N-{4-[3-(2-amino-7,8-dihydropyrido[4,3-d]pyrimidin-6(5H)-yl)-4-methyl-2-oxopyridin-1(2H)-yl]phenyl}-4-methylbenzamide;

N-{4-[3-(2-amino-7,8-dihydropyrido[4,3-d]pyrimidin-6(5H)-yl)-4-methyl-2-oxopyridin-1(2H)-yl]phenyl}-3,4-dimethylbenzamide;

N-{4-[3-(2-amino-7,8-dihydropyrido[4,3-d]pyrimidin-6(5H)-yl)-4-methyl-2-oxopyridin-1(2H)-yl]phenyl}-3-chloro-4-methoxybenzamide;

N-{4-[3-(2-amino-7,8-dihydropyrido[4,3-d]pyrimidin-6(5H)-yl)-4-methyl-2-oxopyridin-1(2H)-yl]phenyl}-2-fluoro-5-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-2-fluoro-5-methylbenzamide;

N-{4-[3-(2-amino-7,8-dihydropyrido[4,3-d]pyrimidin-6(5H)-yl)-4-methyl-2-oxopyridin-1(2H)-yl]phenyl}-5-tert-butylisoxazole-3-carboxamide;

N-{4-[3-(2-amino-7,8-dihydropyrido[4,3-d]pyrimidin-6(5H)-yl)-4-methyl-2-oxopyridin-1(2H)-yl]phenyl}-4-methoxy-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-3-(methylsulfinyl)benzamide;

3-[({4-[3-(2-amino-7,8-dihydropyrido[4,3-d]pyrimidin-6(5H)-yl)-4-methyl-2-oxopyridin-1(2H)-yl]phenyl}amino)carbonyl]benzoic acid;

3-{4-[({4-[3-(2-amino-7,8-dihydropyrido[4,3-d]pyrimidin-6(5H)-yl)-4-methyl-2-oxopyridin-1(2H)-yl]phenyl}amino)carbonyl]phenyl}propanoic acid;

N-{4-[3-(2-amino-7,8-dihydropyrido[4,3-d]pyrimidin-6(5H)-yl)-4-methyl-2-oxopyridin-1(2H)-yl]phenyl}-4-[(4-methylpiperazin-1-yl)methyl]-3-(trifluoromethyl)benzamide;

N-{4-[3-(2-amino-7,8-dihydropyrido[4,3-d]pyrimidin-6(5H)-yl)-4-methyl-2-oxopyridin-1(2H)-yl]phenyl}-4-fluorobenzamide;

N-{4-[3-(2-amino-7,8-dihydropyrido[4,3-d]pyrimidin-6(5H)-yl)-4-methyl-2-oxopyridin-1(2H)-yl]phenyl}-3,4-dimethoxybenzamide;

N-{4-[3-(2-amino-7,8-dihydropyrido[4,3-d]pyrimidin-6(5H)-yl)-4-methyl-2-oxopyridin-1(2H)-yl]phenyl}-2-furamide;

N-{4-[3-(2-amino-7,8-dihydropyrido[4,3-d]pyrimidin-6(5H)-yl)-4-methyl-2-oxopyridin-1(2H)-yl]phenyl}-5-methyl-2-furamide;

4-[3-(2-amino-7,8-dihydropyrido[4,3-d]pyrimidin-6(5H)-yl)-4-methyl-2-oxopyridin-1(2H)-yl]-N-[(3-methyl-2-furyl)methyl]benzamide;

1-{4-[3-(2-amino-7,8-dihydropyrido[4,3-d]pyrimidin-6(5H)-yl)-4-methyl-2-oxopyridin-1(2H)-yl]phenyl}-3-(2-methylphenyl)urea;

1-{4-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea;

3-[3-(2-amino-7,8-dihydropyrido[4,3-d]pyrimidin-6(5H)-yl)-4-methyl-2-oxopyridin-1(2H)-yl]-N-(3-methyl-2-furyl)benzamide;

4-[3-(2-amino-7,8-dihydropyrido[4,3-d]pyrimidin-6(5H)-yl)-4-methyl-2-oxopyridin-1(2H)-yl]-N-(3-methyl-2-furyl)benzamide;

1-{3-[3-(2-amino-7,8-dihydropyrido[4,3-d]pyrimidin-6(5H)-yl)-4-methyl-2-oxopyridin-1(2H)-yl]phenyl}-3-(3-methyl-2-furyl)urea;

4-[3-(2-amino-7,8-dihydropyrido[4,3-d]pyrimidin-6(5H)-yl)-4-methyl-2-oxopyridin-1(2H)-yl]-N-(2-methylphenyl)benzamide;

4-[({[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]amino}carbonyl)amino]butanoic acid;

2-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)benzamide;

2-hydroxyethyl[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]carbamate;

4-({[(6-{4-methyl-1-[4-({[(3-methyl-2-furyl)methyl]amino}carbonyl)phenyl]-2-oxo-1,2-dihydropyridin-3-yl}-5,6,7,8-tetrahydropyrido[4,3-d]pyrimidin-2-yl)amino]carbonyl}amino)butanoic acid;

4-[({[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]amino}carbonyl)amino]butanoic acid;

2-hydroxyethyl[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]carbamate;

3-methyl-N-(4-{4-methyl-3-[2-({[(3-morpholin-4-ylpropyl)amino]carbonyl}amino)-7,8-dihydropyrido[4,3-d]pyrimidin-6(5H)-yl]-2-oxopyridin-1(2H)-yl}phenyl)-2-furamide;

1-(6-{1-[3-(dimethylamino)phenyl]-4-methyl-2-oxo-1,2-dihydropyridin-3-yl}-5,6,7,8-tetrahydropyrido[4,3-d]pyrimidin-2-yl)-3-(3-morpholin-4-ylpropyl)urea;

2-hydroxyethyl (6-{1-[3-(dimethylamino)phenyl]-4-methyl-2-oxo-1,2-dihydropyridin-3-yl}-5,6,7,8-tetrahydropyrido[4,3-d]pyrimidin-2-yl)carbamate;

4-({[(6-{1-[3-(dimethylamino)phenyl]-4-methyl-2-oxo-1,2-dihydropyridin-3-yl}-5,6,7,8-tetrahydropyrido[4,3-d]pyrimidin-2-yl)amino]carbonyl}amino)butanoic acid;

3-(4-{[6-(4-methyl-1-{4-[(2-methylbenzoyl)amino]phenyl}-2-oxo-1,2-dihydropyridin-3-yl)-5,6,7,8-tetrahydropyrido[4,3-d]pyrimidin-2-yl]amino}phenyl)propanoic acid;

N-{4-[3-(2-anilino-7,8-dihydropyrido[4,3-d]pyrimidin-6(5H)-yl)-4-methyl-2-oxopyridin-1(2H)-yl]phenyl}-2-methylbenzamide;

3-{4-[(6-{4-methyl-1-[4-({[(3-methyl-2-furyl)methyl]amino}carbonyl)phenyl]-2-oxo-1,2-dihydropyridin-3-yl}-5,6,7,8-tetrahydropyrido[4,3-d]pyrimidin-2-yl)amino]phenyl}propanoic acid;

4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}-N-[(3-methyl-2-furyl)methyl]benzamide;

4-[3-(2-anilino-7,8-dihydropyrido[4,3-d]pyrimidin-6(5H)-yl)-4-methyl-2-oxopyridin-1(2H)-yl]-N-[(3-methyl-2-furyl)methyl]benzamide;

3-(4-{[6-(4-methyl-1-{4-[(3-methyl-2-furoyl)amino]phenyl}-2-oxo-1,2-dihydropyridin-3-yl)-5,6,7,8-tetrahydropyrido[4,3-d]pyrimidin-2-yl]amino}phenyl)propanoic acid;

N-(4-{3-[2-{[4-(13-hydroxy-5,8,11-trioxa-2-azatridec-1-yl)phenyl]amino}-7,8-dihydropyrido[4,3-d]pyrimidin-6(5H)-yl]-4-methyl-2-oxopyridin-1(2H)-yl}phenyl)-3-methyl-2-furamide;

N-(4-{3-[2-({4-[2-(4-hydroxypiperidin-1-yl)ethyl]phenyl}amino)-7,8-dihydropyrido[4,3-d]pyrimidin-6(5H)-yl]-4-methyl-2-oxopyridin-1(2H)-yl}phenyl)-3-methyl-2-furamide;

N-{4-[3-{2-[(4-{4-[2-(2-hydroxyethoxy)ethyl]piperazin-1-yl}phenyl)amino]-7,8-dihydropyrido[4,3-d]pyrimidin-6(5H)-yl}-4-methyl-2-oxopyridin-1(2H)-yl]phenyl}-3-methyl-2-furamide;

N-{4-[3-(2-anilino-7,8-dihydropyrido[4,3-d]pyrimidin-6(5H)-yl)-4-methyl-2-oxopyridin-1(2H)-yl]phenyl}-3-methyl-2-furamide;

3-{4-[(6-{1-[3-(dimethylamino)phenyl]-4-methyl-2-oxo-1,2-dihydropyridin-3-yl}-5,6,7,8-tetrahydropyrido[4,3-d]pyrimidin-2-yl)amino]phenyl}propanoic acid;

1-[3-(dimethylamino)phenyl]-3-[2-({4-[2-(4-hydroxypiperidin-1-yl)ethyl]phenyl}amino)-7,8-dihydropyrido[4,3-d]pyrimidin-6(5H)-yl]-4-methylpyridin-2(1H)-one;

3-(2-anilino-7,8-dihydropyrido[4,3-d]pyrimidin-6(5H)-yl)-1-[3-(dimethylamino)phenyl]-4-methylpyridin-2(1H)-one;

3-(2-amino-7,8-dihydropyrido[4,3-d]pyrimidin-6(5H)-yl)pyridin-2(1H)-one;

3-(2-amino-7,8-dihydropyrido[4,3-d]pyrimidin-6(5H)-yl)-4-methylpyridin-2(1H)-one.

9. A pharmaceutical composition comprising as active ingredient a therapeutically effective amount of a compound according to claim 1 and a pharmaceutically acceptable adjuvant, diluent or carrier.

\* \* \* \* \*